(12) United States Patent
Okamoto et al.

(10) Patent No.: US 9,872,833 B2
(45) Date of Patent: Jan. 23, 2018

(54) LIPOSOME COMPOSITE BODY

(71) Applicants: National University Corporation Tottori University, Tottori-shi, Tottori (JP); National University Corporation Chiba University, Chiba-shi, Chiba (JP)

(72) Inventors: Yoshiharu Okamoto, Tottori (JP); Yutaka Tamura, Chiba (JP); Akiko Suganami, Chiba (JP); Hideki Hayashi, Chiba (JP); Tomoyuki Madono, Chiba (JP); Hisahiro Matsubara, Chiba (JP); Taro Toyota, Chiba (JP)

(73) Assignees: National University Corporation Tottori University, Tottori (JP); National University Corporation Chiba University, Chiba (JP)

( * ) Notice: Subject to any disclaimer, the term of this patent is extended or adjusted under 35 U.S.C. 154(b) by 737 days.

(21) Appl. No.: 14/349,871

(22) PCT Filed: Oct. 3, 2012

(86) PCT No.: PCT/JP2012/076259
§ 371 (c)(1),
(2) Date: Apr. 4, 2014

(87) PCT Pub. No.: WO2013/051732
PCT Pub. Date: Apr. 11, 2013

(65) Prior Publication Data
US 2014/0369935 A1    Dec. 18, 2014

(30) Foreign Application Priority Data
Oct. 7, 2011    (JP) ................................ 2011-223273

(51) Int. Cl.
*A61K 9/127*    (2006.01)
*A61K 41/00*    (2006.01)
(Continued)

(52) U.S. Cl.
CPC ............ *A61K 9/127* (2013.01); *A61K 31/403* (2013.01); *A61K 31/675* (2013.01);
(Continued)

(58) Field of Classification Search
CPC ...................................................... A61K 9/127
See application file for complete search history.

(56) References Cited

U.S. PATENT DOCUMENTS 5,595,756 A * 1/1997 Bally .................. A61K 9/1272
264/4.1
2007/0231375 A1    10/2007 Tsai et al.
(Continued)

FOREIGN PATENT DOCUMENTS

CN       103038629 A     4/2013
JP     2007-277218 A    10/2007
(Continued)

OTHER PUBLICATIONS

Supplementary European Search Report dated May 18, 2015, in EP 12838190.2.
Office Action dated Nov. 2, 2015 in CN 201280049278.7.

*Primary Examiner* — Gollamudi Kishore
(74) *Attorney, Agent, or Firm* — Foley & Lardner LLP

(57) ABSTRACT

An object of the present invention is to provide a drug delivery system capable of sustainedly releasing a drug noninvasively at any given point in time. The present invention relates to a liposome complex comprising a liposome membrane-constituting substance bonded to a light-absorbing compound having an absorption wavelength in the near-infrared region, selected from the group consisting of indocyanine green dyes, phthalocyanine dyes, squarylium dyes, croconium dyes, and diimmonium dyes.

9 Claims, 32 Drawing Sheets
(25 of 32 Drawing Sheet(s) Filed in Color)

(51) Int. Cl.
*A61K 49/00* (2006.01)
*A61K 31/403* (2006.01)
*A61K 31/675* (2006.01)

(52) U.S. Cl.
CPC ...... *A61K 41/0052* (2013.01); *A61K 41/0057* (2013.01); *A61K 49/0021* (2013.01); *A61K 49/0034* (2013.01); *A61K 49/0052* (2013.01); *A61K 49/0084* (2013.01)

(56) References Cited

U.S. PATENT DOCUMENTS

| | | | | |
|---|---|---|---|---|
| 2008/0260648 | A1* | 10/2008 | Takeyama | A61K 9/1694 424/9.32 |
| 2009/0062719 | A1* | 3/2009 | Neuberger | A61K 41/0071 604/20 |
| 2010/0034749 | A1* | 2/2010 | Schulze | A61K 9/1272 424/9.6 |
| 2010/0069824 | A1 | 3/2010 | Okamoto et al. | |
| 2011/0002849 | A1 | 1/2011 | Danikas et al. | |
| 2013/0129631 | A1 | 5/2013 | Hayashi et al. | |

FOREIGN PATENT DOCUMENTS

| | | |
|---|---|---|
| JP | 2010-069001 A | 10/2007 |
| JP | 2010-266295 A | 11/2010 |
| JP | 2011-513211 A | 4/2011 |
| WO | WO 00/41726 A3 | 7/2000 |
| WO | 02/44396 * | 6/2002 |
| WO | WO 2004/004769 A1 | 1/2004 |
| WO | WO 2005/021012 A1 | 3/2005 |
| WO | WO 2009/145243 A1 | 12/2009 |
| WO | WO 2011/044671 A1 | 4/2011 |

* cited by examiner

Particle diameter: 200nm

●, ▲, ■ : Various agents

Rat F344/Jc1 34-36 weeks 9L Glioma cell Tumor diameter About 30mm

Rat
 F344/Jc1 (34-36 weeks)
 9L Glioma cell
 Tumor diameter About 30mm

Light source
 Wavelength 600-1600nm
 Output 5W
 Irradiation 20min
 Apparatus Hyper5000 (Tokyo Iken Co., Ltd.)

LIPOSOME COMPOSITE BODY

CROSS-REFERENCE TO RELATED APPLICATIONS

This application is a National Stage application of PCT/JP2012/076259, filed Oct. 3, 2012, which claims priority from Japanese application JP 2011-223273, filed Oct. 7, 2011.

TECHNICAL FIELD

The present invention relates to a liposome complex comprising a liposome membrane-constituting substance bonded to a light-absorbing compound and an agent, which can be used for a drug delivery system or the like.

BACKGROUND ART

A drug delivery system (DDS) is a technique for effectively and locally delivering a drug to a targeted affected area (organ, tissue, cells, pathogen, or the like). Macromolecules and fine particles easily flow out of the blood vessel in tumor tissue because blood vessel permeability is significantly enhanced compared to in normal tissue. Substances reaching tumor tissue accumulate because the lymphoid system is not developed. Such a characteristic is called an EPR effect and is an important factor in passive targeting to cancer cells. However, although the EPR effect has enabled the cancer tissue-selective delivery/accumulation of a drug carrier administered into the blood vessel, it remains to be a challenge to sustainedly release the agent contained in the carrier effectively.

Meanwhile, attention has been given in recent years to hyperthermia chemotherapy and photodynamic therapy utilizing the heat-generating effect and the active oxygen-producing effect (PDT effect) of a dye having an absorption wavelength in the infrared region. These therapies utilize the transmission properties of near infrared light in the living body and a compound capable of absorbing near infrared light; for example, Patent Document 1 (JP 2010-69001 A) discloses photodynamic hyperthermia chemotherapy using indocyanine green (ICG) as a photosensitive dye agent to utilize its heat-generating and active oxygen-producing effects. This document describes that the injection of cis-platin and ICG into the site of tumor tissue of an animal followed by light irradiation resulted in no identification of the recurrence and metastasis of the tumor even after a lapse of 1 year after treatment.

Patent Document 2 (WO 00/41726) also discloses transdermal photodynamic therapy using a photosensitizer such as ICG. According to the invention of this document, a photosensitizing agent delivery system includes a liposome delivery system comprising a photosensitizing agent. The liposome delivery system adopts a form in which the photosensitizing agent is administered in the form of a liposome formulation (i.e., uses the photosensitizing agent by including it in a liposome). However, this document only describes the use of the photosensitizing agent in tumor tissue and does not disclose aspects such as the co-administration of an anti-cancer agent.

Patent Document 3 (JP 2007-277218 A) discloses a liposome composition comprising a hydrophilic drug included in the hydrophilic layer of the liposome and a hydrophobic photosensitive substance included in the lipid bilayer of the liposome, wherein the liposome is induced to release the hydrophilic drug by a photodynamic effect under irradiation by a light source. However, disclosed as the photosensitive substance is only porphyrin, and porphyrin has side effects including hypersensitivity such as solar dermatitis (pruritic rash, erythema, or blister); digestive symptoms such as nausea, gastrointestinal problems, diarrhea, stomach ache, and abdominal discomfort; and other side effects such as pigmentation, cardiac palpitation, feeling of heat, physical discomfort, hot flush, and black stool.

Patent Document 4 (JP 2010-266295 A) discloses a fluorescent tissue marker having a vesicle cluster obtained by including vesicles formed by the combination of a phospholipid and a near-infrared fluorescent dye such as indocyanine green in a hydrophilic solvent and forming and aggregating a plurality of capsules using an emulsifier. However, it is intended to be used as a fluorescent tissue marker, and the application thereof to photodynamic hyperthermia chemotherapy or the inclusion of an agent in a liposome is not contemplated.

CITATION LIST

Patent Document

[Patent Document 1] JP 2010-69001 A
[Patent Document 2] WO 00/41726
[Patent Document 3] JP 2007-277218 A
[Patent Document 4] JP 2010-266295 A

SUMMARY OF INVENTION

Technical Problem

Thus, these conventional methods have only an object of causing a photosensitizer such as ICG to act directly on an affected area, and remain to have a problem of the control of sustained release of an agent. Accordingly, an object of the present invention is to provide a drug delivery system capable of noninvasive sustained release of a drug at any given point in time.

Solution to Problem

As a result of intensive studies for solving the above problems, the present inventors have found that an agent can be sustainedly released into an affected area noninvasively at any time by including the agent in a liposome whose lipid bilayer membrane has a near-infrared absorbing dye, followed by light irradiation, thereby accomplishing the present invention. Specifically, the present invention encompasses the following inventions.

[1] A liposome complex comprising a liposome membrane-constituting substance bonded to a light-absorbing compound having an absorption wavelength in the near-infrared region, selected from the group consisting of indocyanine green dyes, phthalocyanine dyes, squarylium dyes, croconium dyes, and diimmonium dyes, and also comprising an agent in the liposome.

[2] The liposome complex according to [1] above, wherein the liposome membrane-constituting substance comprises a lipid.

[3] The liposome complex according to [1] above, wherein the liposome membrane-constituting substance bonded to a light-absorbing compound is represented by formula (I) below:

$$A\text{-}(CH_2)_a\text{-}B_1\text{-}(CH_2)_b\text{-}B_2\text{-}D\text{-}E_1 \quad (I)$$

wherein A represents a light-absorbing compound;
$B_1$ and $B_2$ each independently represent —$CH_2$—, —O—, —S—, —NH—, —CO—, —COO—, —OCO—, —NHCO—, —CONH—, —SO$_2$—, —SO$_2$NH—, —NHSO$_2$—, —PO$_4$M- (where M represents an alkali metal ion), or —(CH$_2$CH$_2$O)$_c$— (where c represents an integer of 1 to 10);

D represents —CHE$_2$-, —NE$_2$-, —C$_6$H$_4$E$_2$-, —CH$_2$CH(OCOE$_2$)-CH$_2$OCO—, or —CHE$_2$-CH$_2$OCO—;

E$_1$ represents a substituted or unsubstituted hydrocarbon group having 8 to 18 carbon atoms;

E$_2$ represents hydrogen or a substituted or unsubstituted hydrocarbon group having 8 to 18 carbon atoms; and a represents an integer of 0 to 4 and b represents an integer of 0 to 6.

[4] The liposome complex according to [3] above, wherein B$_1$ and B$_2$ each independently represent —CH$_2$—, —CH=CH—, —O—, or —S—; and D represents —CHE$_2$- (where E$_2$ is as described in [3] above).

[5] The liposome complex according to [4] above, wherein B$_1$ and B$_2$ each represent —CH$_2$—.

[6] The liposome complex according to any one of [1] to [5] above, used in photothermal therapy and/or photodynamic therapy.

[7] The liposome complex according to any one of [1] to [6] above, used in fluorescent imaging.

Advantageous Effects of Invention

According to the present invention, a desired agent can be caused to noninvasively act on an affected area at any given point in time.

BRIEF DESCRIPTION OF DRAWINGS

The application file contains at least one drawing executed in color. Copies of this patent application publication with color drawing(s) will be provided by the Office upon request and payment of the necessary fee.

DESCRIPTION OF EMBODIMENTS

Figure 1:
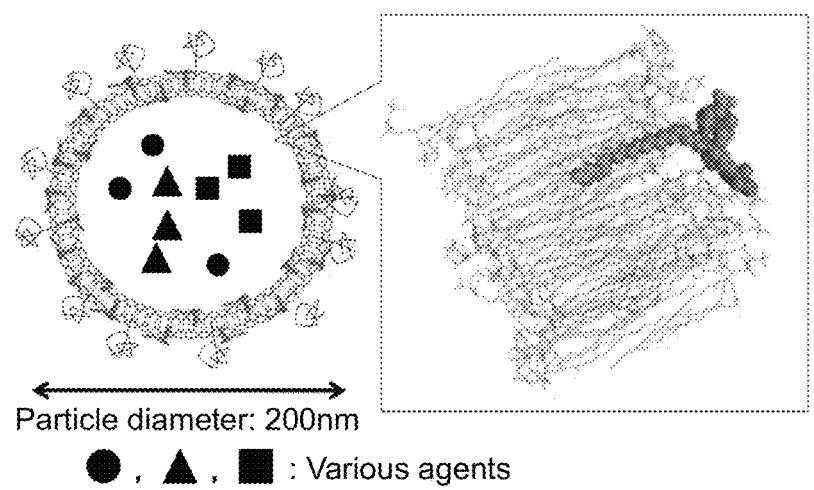
FIG. 1 is a schematic view of a liposome complex of the present invention.

The present invention will be described below in detail.

The liposome complex of the present invention comprises a liposome membrane-constituting substance bonded to a light-absorbing compound having an absorption wavelength in the near-infrared region, selected from the group consisting of indocyanine green dyes, phthalocyanine dyes, squarylium dyes, croconium dyes, and diimmonium dyes, and also comprises an agent in the liposome.

As used herein, "light-absorbing compound" is a compound generating sufficient heat to split the liposome by absorbing light in the near-infrared region and preferably, further generating sufficient heat to produce singlet oxygen and/or kill tumor cells. "Absorption wavelength in the near-infrared region" is 700 to 1,400 nm, preferably 800 to 1,000 nm, particularly preferably 800 to 900 nm, as the maximum absorption wavelength of the light-absorbing compound.

As used herein, "liposome membrane-constituting substance" is not particularly limited provided that it does not inhibit the formation of a lipid bilayer membrane, and examples thereof include lipids, membrane stabilizers, antioxidants, charged substances, and membrane proteins.

Examples of the lipids include phospholipids, glycolipids, sterols, and saturated or unsaturated fatty acids.

Examples of the phospholipids include phosphatidylcholines (for example, dioleoylphosphatidylcholine, dilauroylphosphatidylcholine, dimyristoylphosphatidylcholine, dipalmitoylphosphatidylcholine, and distearoylphosphatidylcholine), phosphatidylglycerols (for example, dioleoylphosphatidylglycerol, dilauroylphosphatidylglycerol, dimyristoylphosphatidylglycerol, dipalmitoylphosphatidylglycerol, and distearoylphosphatidylglycerol), phosphatidylethanolamines (for example, diolcoylphosphatidylethanolamine, dilauroylphosphatidylethanolamine, dimyristoylphosphatidylethanolamine, dipalmitoylphosphatidylethanolamine, and distearoylphosphatidylethanolamine), phosphatidylserine, phosphatidylinositol, phosphatidic acid, cardiolipin, sphingomyelin, egg yolk lecithin, soybean lecithin, and hydrogenated products thereof.

Examples of the glycolipids include glyceroglycolipids (for example, sulfoxyribosyl glyceride, diglycosyl diglyceride, digalactosyl diglyceride, galactosyl diglyceride, and glycosyl diglyceride) and sphingoglycolipids (for example, galactosyl cerebroside, lactosyl cerebroside and ganglioside).

Examples of the sterols include animal-derived sterols (for example, cholesterol, cholesterol succinate, lanosterol, dihydrolanosterol, desmosterol and dihydrocholesterol), plant-derived sterols (phytosterols) (for example, stigmasterol, sitosterol, campesterol and brassicasterol), and microorganism-derived sterols (for example, thymosterol and ergosterol).

Examples of the saturated or unsaturated fatty acids include saturated or unsaturated fatty acids having 12 to 20 carbon atoms, such as palmitic acid, oleic acid, stearic acid, arachidonic acid, and myristic acid.

The membrane stabilizer is an optional liposome membrane component capable of being added for the physical or chemical stabilization of the liposome membrane or the control of the liposome membrane fluidity. Examples of the membrane stabilizer include sterols, and glycerin or fatty acid esters thereof.

Specific examples of the sterols include the same as those mentioned above, and examples of the fatty acid esters of glycerin include triolein and trioctanoin.

The antioxidant is an optional liposome membrane component capable of being added for the prevention of the oxidization of the liposome membrane, and examples thereof include tocopherol, propyl gallate, ascorbyl palmitate, and butylated hydroxytoluene.

The charged substance is an optional liposome membrane component capable of being added to impart a positive charge or a negative charge to the liposome membrane; examples of the charged substance imparting a positive charge include saturated or unsaturated aliphatic amines such as stearylamine and oleylamine and saturated or unsaturated cationic synthetic lipids such as dioleoyltrimethylammoniumpropane, and examples of the charged substance imparting a negative charge include dicetyl phosphate, cholesteryl hemisuccinate, phosphatidylserine, phosphatidylinositol, and phosphatidic acid.

The membrane protein is an optional liposome membrane component capable of being added to maintain the structure of the liposome membrane or to impart functionality to the liposome membrane, and examples thereof include membrane extrinsic proteins and integral membrane proteins.

The liposome membrane-constituting substance "bonded to a light-absorbing compound" represents a compound in which the liposome membrane-constituting substance is covalently bonded to a light-absorbing compound, and preferred examples of the "liposome membrane-constituting substance bonded to a light-absorbing compound" include a compound represented by formula (I) above.

Examples of the alkali metal ion represented by M in the formula (I) include sodium ion and potassium ion.

Examples of the hydrocarbon group having 8 to 18 carbon atoms represented by $E_1$ or $E_2$ in the formula (I) include alkanes, alkenes (the number of whose double bonds is preferably 2 or less), and alkynes (the number of whose triple bonds is preferably 2 or less) each having 8 to 18 carbon atoms, preferably 12 to 18 carbon atoms, more preferably alkanes, alkenes, and alkynes each having 14 to 18 carbon atoms. These hydrocarbon groups may each be substituted, for example, by a halogen atom or alkoxy having 1 to 6 carbon atoms.

In the formula (I), a represents an integer of 0 to 4, preferably 0 to 2. b represents an integer of 0 to 6, preferably 0 to 2. c represents an integer of 1 to 10, preferably 1 to 4, more preferably 1 to 2.

In the formula (I), the adoption of the above-described groups as $B_1$ and $B_2$ enables the stabilization of the molecule itself by the affinity thereof to phosphate groups on the liposome surface. The adoption of any of the above-described groups as D enables anchoring to the hydrophobic region of the liposome. The adoption of the above-described groups as $E_1$ and $E_2$ enables the sharp increase or decrease of membrane fluidity with an increase in temperature without decreasing the membrane fluidity at on the order of room temperature to body temperature. a and b can be set to the above-described range to cause the dye to be separated by several angstroms from the side chain structure to reduce the influence of the electrical chemical state of the liposome surface on the generation of singlet oxygen.

The "liposome complex" of the present invention contains the liposome membrane-constituting substance bonded to a light-absorbing compound in an amount of typically 0.01 to 50% (molar ratio), preferably 0.1 to 5% (molar ratio), more preferably 0.1 to 1% (molar ratio) based on the total blending amount of the substances constituting the lipid bilayer membrane. Lipid is an essential component as a substance constituting the lipid bilayer membrane, and the bending amount thereof is typically 20 to 99.9% (molar ratio), preferably 50 to 99% (molar ratio), more preferably 80 to 95% (molar ratio) based on the total blending amount of the substances constituting the lipid bilayer membrane. To stabilize the lipid membrane, it is preferable to further add cholesterol and the like. Cholesterol and the like can be used in a blending amount in such a range that the object of the present invention is not impaired.

To stabilize the liposome in vivo, the external surface of the liposome can be modified using a hydrophilic polymer. Examples of the hydrophilic polymer include polyethylene glycol, polymethylethylene glycol, polyhydroxypropylene glycol, polypropylene glycol, polymethylpropylene glycol, and polyhydroxypropylene oxide. Particularly preferred is polyethylene glycol. The blending amount thereof is typically 0.01 to 10% (molar ratio), preferably 0.1 to 1% (molar ratio) based on the total blending amount of the substances constituting the lipid bilayer membrane.

To deliver the liposome complex to a target site, a liposome membrane-constituting substance bonded to a substance (cell membrane-binding substance) capable of binding to a receptor or an antigen present on the cell membrane surface may be used as a constituent of the lipid bilayer membrane of the liposome; examples of the cell membrane-binding substance include transferrin, insulin, folic acid, hyaluronic acid, antibodies or fragments thereof, sugar chains, growth factors, and apolipoproteins.

The liposome complex of the present invention includes an agent in the liposome. The agent is not particularly limited and may be an agent such as an anti-cancer agent, a protein, a peptide, a nucleic acid, or the like. The anti-cancer agent may be one well known to those of ordinary skill in the art, and examples thereof include the following compounds: alkylating agents such as cyclophosphamide, melphalan, ranimustine, ifosfamide, and nitrogen mustard-N-oxide hydrochloride; antimetabolites such as 6-mercaptopurine, riboside, enocitabine, carmofur, cytarabine, cytarabine ocfosfate, tegafur, 5-fluorouracil, doxifluuridine, doxifluridine, hydroxycarbamide, methotrexate, and mercaptopurine; antitumor antibiotic preparations such as actinomycin D, aclarubicin hydrochloride, epirubicin hydrochloride, idarubicin hydrochloride, doxorubicin hydrochloride, daunorubicin hydrochloride, pirarubicin hydrochloride, zinostatin stimalamer, bleomycin sulfate, bleomycin hydrochloride, mitomycin C, neocarzinostatin, and peplomycin sulfate; antitumor plant ingredient preparations such as etoposide, irinotecan hydrochloride, docetaxel hydrate, vincristine sulfate, vindesine sulfate, vinblastine sulfate, and paclitaxel; and others such as aceglatone, ubenimex, cisplatin, sizofiran, sobuzoxane, krestin, toremifene citrate, medroxyprogesterone acetate, tamoxifen citrate, carboplatin, fadrozole hydrochloride hydrate, procarbazine hydrochloride, mitoxantrone hydrochloride, L-asparaginase, tretinoin, nedaplatin, picibanil, flutamide, pentostatin, porfimer sodium, and lentinan.

Examples of the liposome membrane-constituting substance bonded to the indocyanine green dyes as the light-absorbing compound include a compound represented by formula (II-1) below:

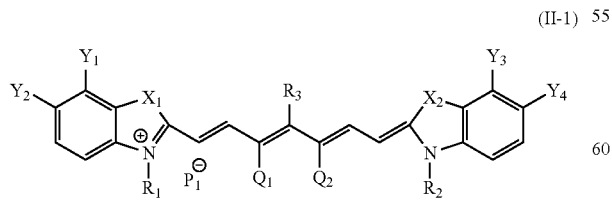

(II-1)

wherein $X_1$ and $X_2$ each represent —C(CH$_3$)$_2$—, O, or S; $Y_1$ and $Y_3$ each represent hydrogen or OCH$_3$ and $Y_2$ and $Y_4$ each represent hydrogen, or $Y_1$ and $Y_2$, and $Y_3$ and $Y_4$ each optionally together form a benzene ring fused with a ring to which they are bound; $Q_1$ and $Q_2$ each represent hydrogen or are optionally bonded to form a 6-membered ring; any one of $R_1$ to $R_3$ represents —(CH$_2$)$_a$-B$_1$-(CH$_2$)$_b$-B$_2$-D-E$_1$ where the symbols have the same meaning as those in the formula (I); $P_1$ represents chloride ion, bromide ion, or iodide ion as a monovalent anion; and $R_1$ to $R_3$ each represent a group selected from the group consisting of the following groups:

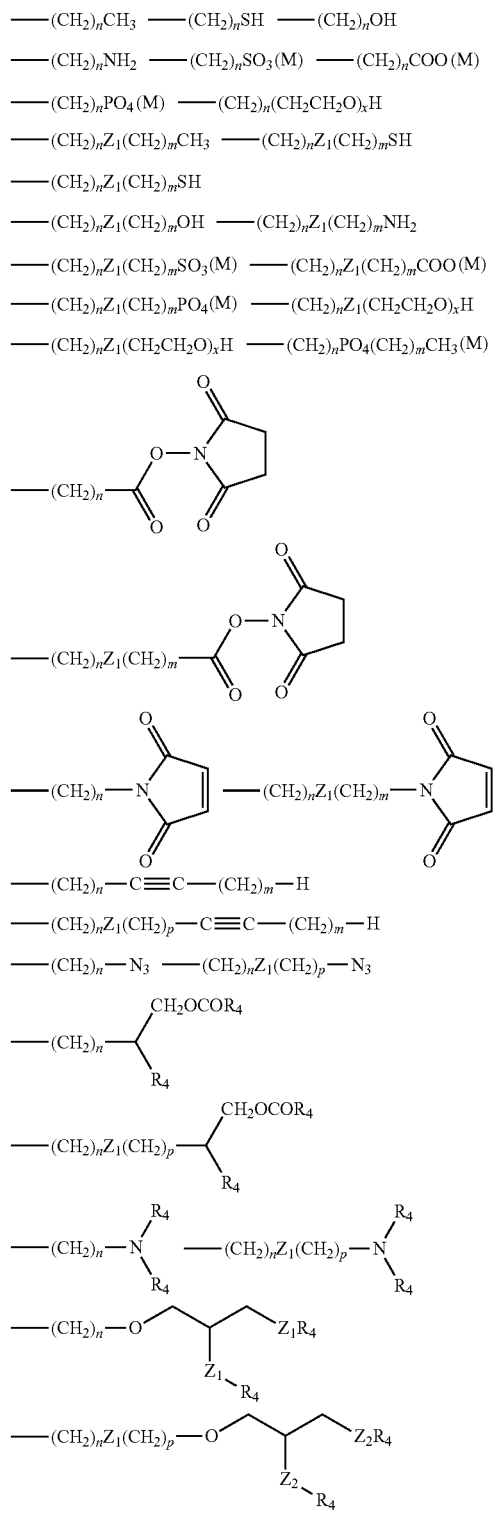

-continued

—(CH$_2$)$_n$—O—PO$_2$—O—CH$_2$CH(Z$_1$R$_4$)CH$_2$Z$_1$R$_4$
(P$_2$)

—(CH$_2$)$_n$Z$_1$(CH$_2$)$_p$—O—PO$_2$—O—CH$_2$CH(Z$_2$R$_4$)CH$_2$Z$_2$R$_4$
(P$_2$)

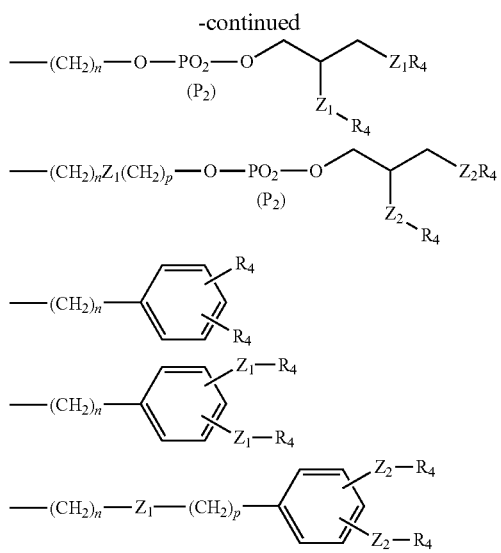

where Z$_1$ or Z$_2$ represents —O—, —NH—, —S—, —SO$_2$—, —CH=CH—, —SO$_2$NH—, —NHSO$_2$—, —CONH—, —NHCO—, —CO—, —COO—, —OCO—, or —C$_6$H$_4$—; P$_2$ represents hydrogen ion, lithium ion, sodium ion, or potassium ion as a monovalent cation; M represents hydrogen ion, lithium ion, sodium ion, or potassium ion as a monovalent cation; R$_4$ represents an alkane, an alkene, or an alkyne having 1 to 18, preferably 4 to 10, carbon atoms; n or m represents an integer of 0 to 22, preferably 0 to 4; l represents an integer of 1 to 22, preferably 1 to 4; p represents an integer of 0 to 17, preferably 0 to 2; and x represents an integer of 2 to 2,000, preferably 2 to 150.

Examples of the liposome membrane-constituting substance bonded to the phthalocyanine dyes as the light-absorbing compound include a compound represented by formula (II-2) below:

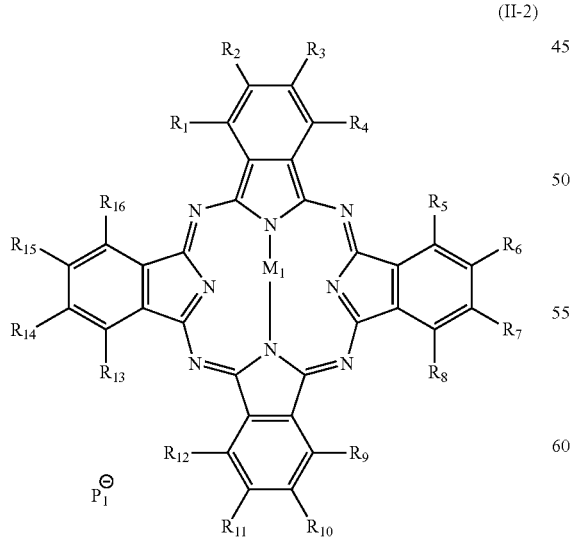

(II-2)

wherein R$_1$ to R$_{16}$ each represent any of the following groups:

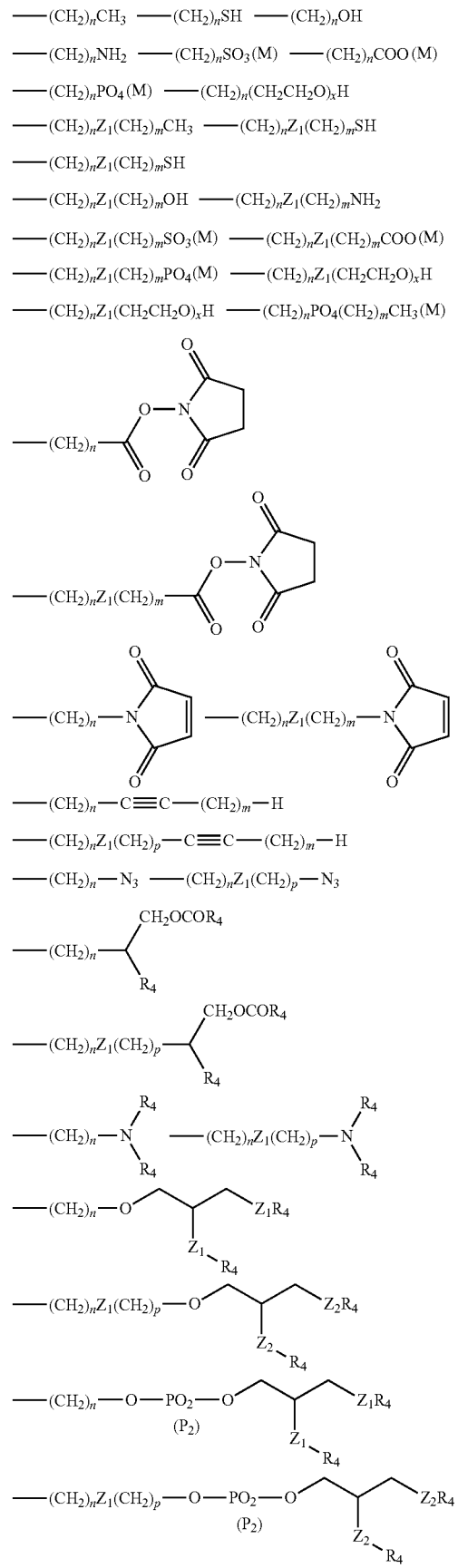

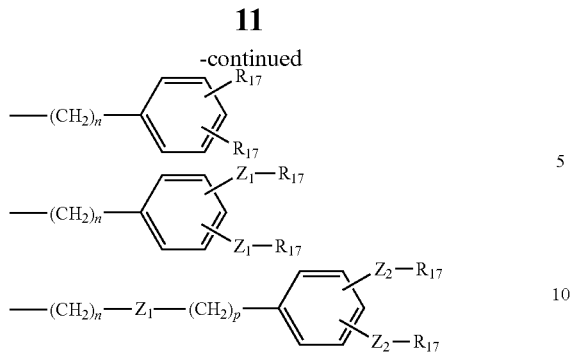

where at least one of $R_1$ to $R_{16}$ represents —$(CH_2)_a$-$B_1$-$(CH_2)_b$-$B_2$-D-$E_1$ where the symbols have the same meaning as those in the formula (I); $Z_1$ or $Z_2$ represents —O—, —NH—, —S—, —SO$_2$—, —CH=CH—, —SO$_2$NH—, —NHSO$_2$—, —CONH—, —NHCO—, —CO—, —COO—, —OCO—, or —C$_6$H$_4$—; $R_{17}$ represents an alkane, an alkene, or an alkyne having 1 to 24, preferably 6 to 18, carbon atoms; $P_1$ represents chloride ion, bromide ion, or iodide ion as a monovalent anion; $M_1$ represents hydrogen (2 atoms), or zinc ion, copper ion, iron ion, magnesium ion, cobalt ion, tin ion, titanium ion, or nickel ion as a cation; M represents hydrogen ion, lithium ion, sodium ion, or potassium ion as a monovalent cation; $P_2$ represents hydrogen ion, lithium ion, sodium ion, or potassium ion as a monovalent cation; n or m represents an integer of 0 to 22, preferably 0 to 4; l represents an integer of 1 to 22, preferably 0 to 4; p represents an integer of 0 to 17, preferably 0 to 2; and x represents an integer of 2 to 2,000, preferably 2 to 150.

Examples of the liposome membrane-constituting substance bonded to the squarylium dyes as the light-absorbing compound include a compound represented by formula (II-3) below:

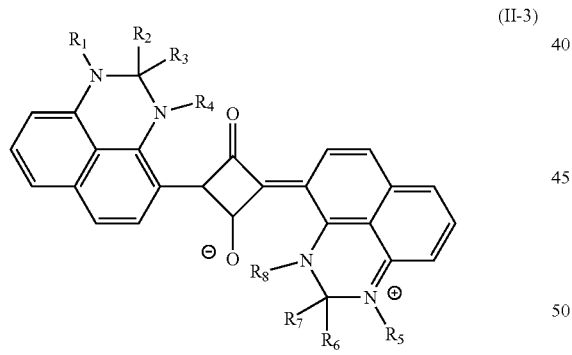

wherein $R_1$ to $R_8$ each represent any of the following groups:

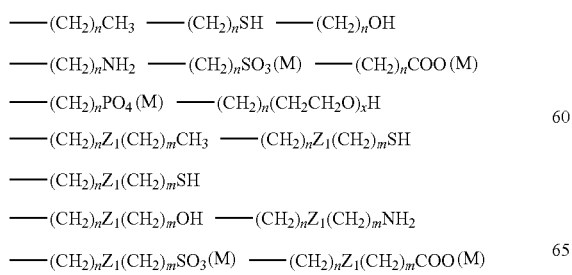

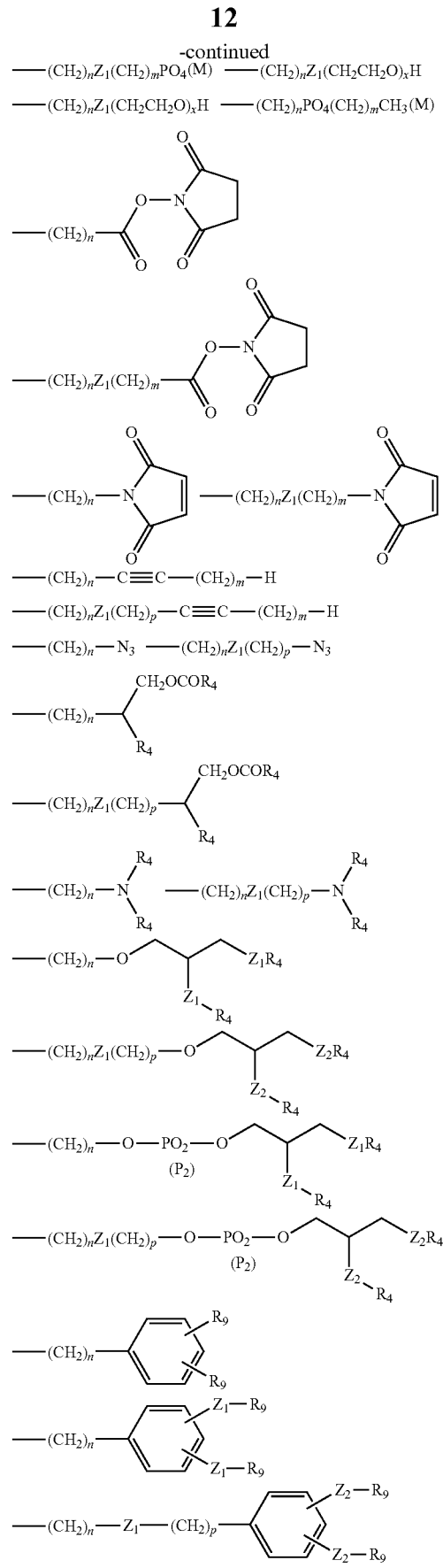

where at least one of $R_1$ to $R_8$ represents —$(CH_2)_a$-$B_1$-$(CH_2)_b$-$B_2$-D-$E_1$ where the symbols have the same meaning as those in the formula (I); $Z_1$ or $Z_2$ represents —O—, —NH—, —S—, —SO$_2$—, —CH=CH—, —SO$_2$NH—, —NHSO$_2$—, —CONH—, —NHCO—, —CO—, —COO—, —OCO—, or —C$_6$H$_4$—; $R_9$ represents an alkane, an alkene, or an alkyne having 1 to 24, preferably 6 to 18, carbon atoms; M represents hydrogen ion, lithium ion, sodium ion, or potassium ion as a monovalent cation; $P_2$ represents hydrogen ion, lithium ion, sodium ion, or potassium ion as a monovalent cation; n or m represents an integer of 0 to 22, preferably 0 to 4; l represents an integer of 1 to 22, preferably 1 to 4; p represents an integer of 0 to 17, preferably 0 to 2; and x represents an integer of 2 to 2,000, preferably 2 to 150.

Examples of the liposome membrane-constituting substance bonded to the croconium dyes as the light-absorbing compound include a compound represented by formula (II-4) below:

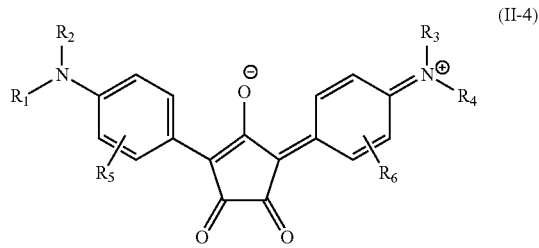

(II-4)

wherein $R_1$ to $R_6$ each represent any of the following groups:

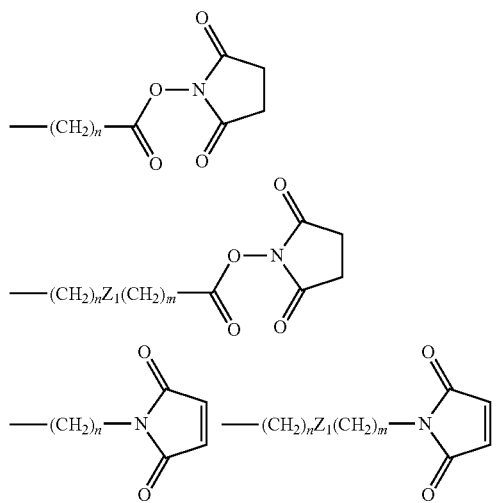

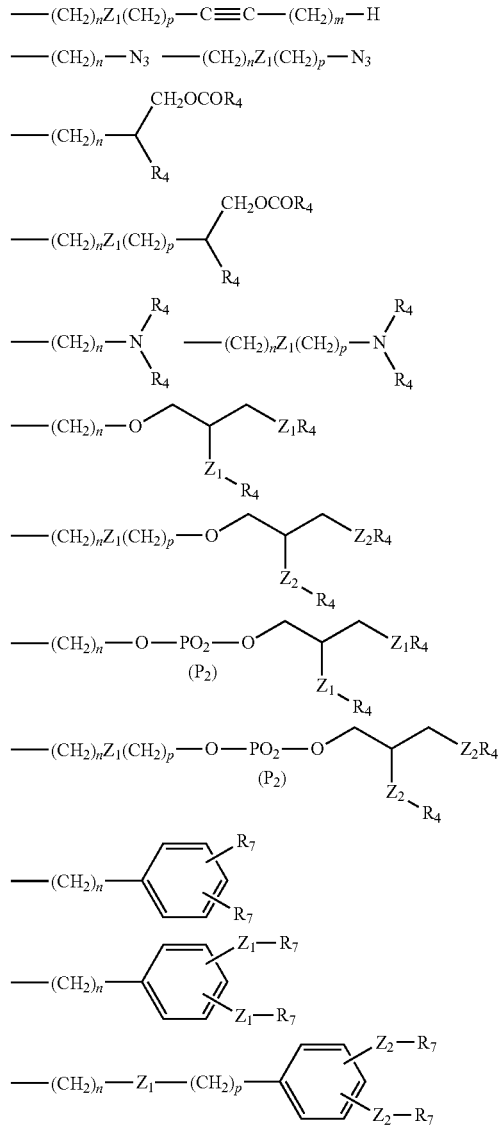

where at least one of $R_1$ to $R_6$ represents —$(CH_2)_a$-$B_1$-$(CH_2)_b$-$B_2$-D-$E_1$ where the symbols have the same meaning as those in the formula (I); $Z_1$ or $Z_2$ represents —O—, —NH—, —S—, —SO$_2$—, —CH=CH—, —SO$_2$NH—, —NHSO$_2$—, —CONH—, —NHCO—, —CO—, —COO—, —OCO—, or —C$_6$H$_4$—; $R_7$ represents an alkane, an alkene, or an alkyne having 1 to 24, preferably 6 to 18, carbon atoms; M represents hydrogen ion, lithium ion, sodium ion, or potassium ion as a monovalent cation; $P_2$ represents hydrogen ion, lithium ion, sodium ion, or potassium ion as a monovalent cation; n or m represents an integer of 0 to 22, preferably 0 to 4; l represents an integer of 1 to 22, preferably 1 to 4; p represents an integer of 0 to 17, preferably 0 to 2; and x represents an integer of 2 to 2,000, preferably 2 to 150.

Examples of the liposome membrane-constituting substance bonded to the diimmonium dyes as the light-absorbing compound include a compound represented by formula (II-5) below:

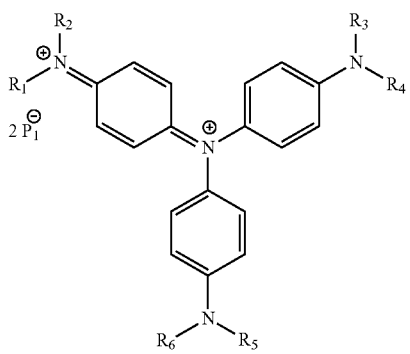

(II-5)

wherein $R_1$ to $R_6$ each represent any of the following groups:

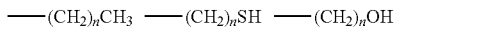
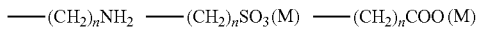
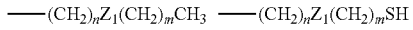
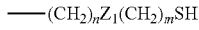
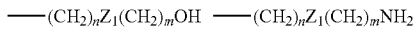
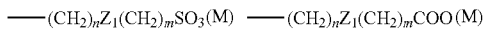
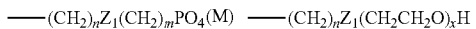
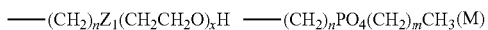
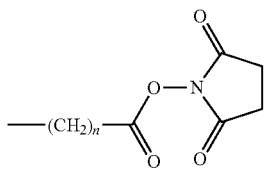
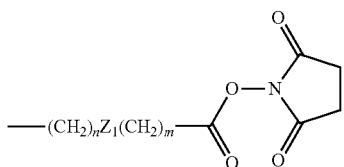
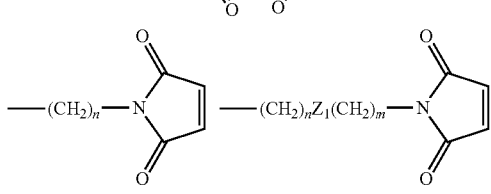
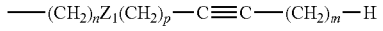
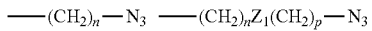
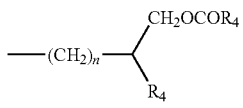
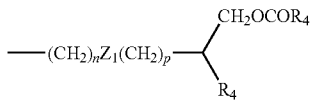

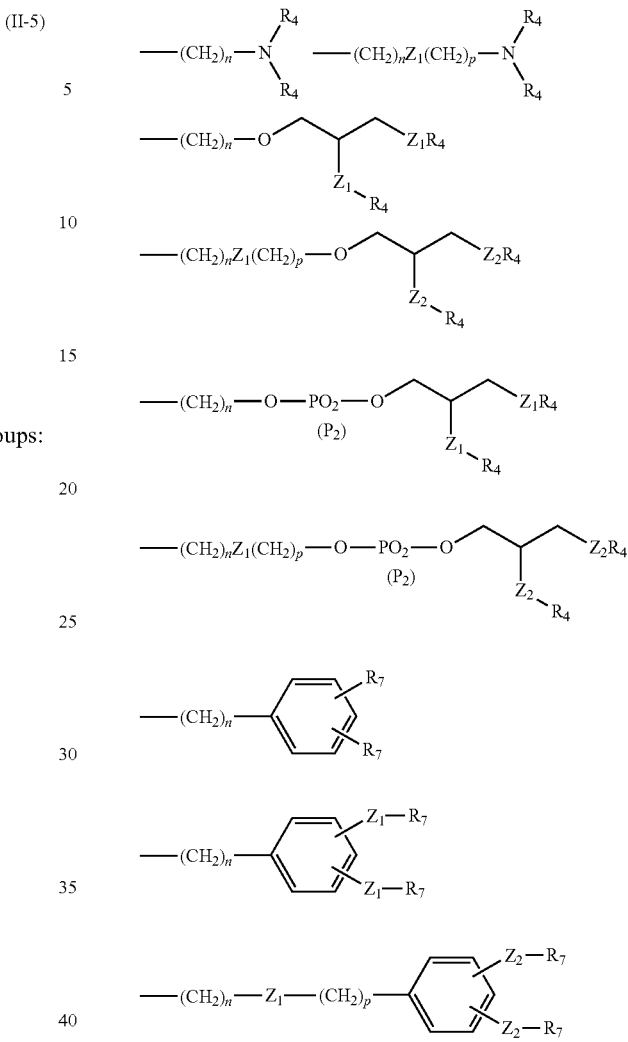

where at least one of $R_1$ to $R_6$ represents —$(CH_2)_a$-$B_1$-$(CH_2)_b$-$B_2$-D-$E_1$ where the symbols have the same meaning as those in the formula (I); $Z_1$ or $Z_2$ represents —O—, —NH—, —S—, —SO$_2$—, —CH=CH—, —SO$_2$NH—, —NHSO$_2$—, —CONH—, —NHCO—, —CO—, —COO—, —OCO—, or —C$_6$H$_4$—; $R_7$ represents an alkane, an alkene, or an alkyne having 1 to 24, preferably 6 to 18, carbon atoms; $P_1$ represents chloride ion, bromide ion, or iodide ion as a monovalent anion; M represents hydrogen ion, lithium ion, sodium ion, or potassium ion as a monovalent cation; $P_2$ represents hydrogen ion, lithium ion, sodium ion, or potassium ion as a monovalent cation; n or m represents an integer of 0 to 22, preferably 0 to 4; l represents an integer of 1 to 22, preferably 1 to 4; p represents an integer of 0 to 17, preferably 0 to 2; and x represents an integer of 2 to 2,000, preferably 2 to 150.

The indocyanine green dye represented by the formula (II-1) can be synthesized according to a well-known method as described, for example, in WO2011/152046, WO1995/007888, JP 09-124599 A (1997), JP 03-171136 A (1991), or J. Org. Chem. (1995) 60, 2391.

Specifically, it can be synthesized according to the following scheme.

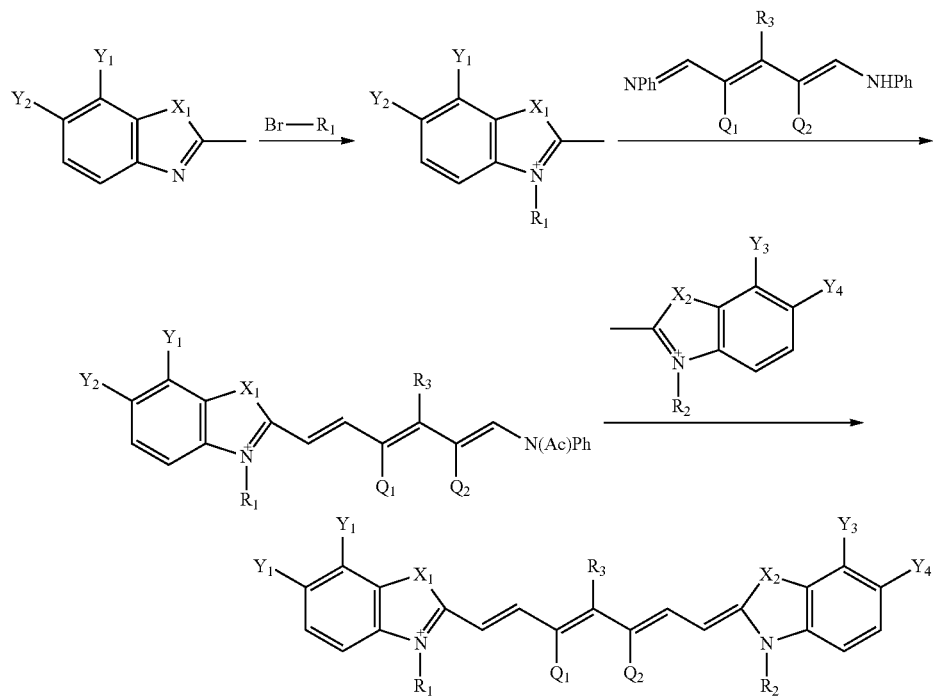

wherein the symbols have the same meaning as those in the formula (II-1).

An indole derivative (for example, 2,3,3-trimethyl-4,5-benzo-3H-indole) can be alkylated with a bromine compound (Br—$R_1$) to make an N—$R_1$-substituted indole derivative, which is then reacted with a glutaconaldehydedianil for linkage to the hexatriene chain, followed by coupling an N—$R_2$-substituted indole derivative thereto to provide a desired indocyanine green dye.

The phthalocyanine dye represented by the formula (II-2) can be synthesized according to a well-known method as described, for example, in JP 2004-18561 A.

The squarylium dye represented by the formula (II-3) can be synthesized according to a well-known method as described, for example, in JP 2011-69846 A.

The croconium dye represented by the formula (II-4) can be synthesized according to a well-known method as described, for example, in JP 2007-31644 A.

The diimmonium dye represented by the formula (II-5) can be synthesized according to a well-known method as described, for example, in "11. Jiimoniumukei kagohbutsu o mochiita kinsekigaisenkyushu fuirumu no taikyusei kohjoh (Improvement in Durability of Near-infrared Light-absorbing Film Using Diimmonium Compound)" Reports Res. Lab. Asahi Glass Co., Ltd. (2005) 55, 67-71.

The liposome complex of the present invention can be produced using any method known in the art; for example, it can be produced by dissolving a liposome membrane-constituting substance bonded to a light-absorbing compound, a phospholipid, and an agent in a suitable organic solvent, and drying the resultant, followed by dispersion in an aqueous solution and repeated passage through a filter. Alternatively, it may be produced by ultrasonication or a reverse phase evaporation method as known in the art.

By way of example, in a suitable organic solvent are dissolved a liposome membrane-constituting substance bonded to a light-absorbing compound, a phospholipid (for example, yolk lecithin containing phosphatidylcholine), a lipid (for example, cholesterol), and a phospholipid derivative of a hydrophilic polymer (for example, a polyethylene glycol-modified phospholipid), and the organic solvent is removed therefrom to form a thin membrane, followed by adding an aqueous solution containing an agent. The aqueous solution may be any aqueous solution provided that it is a physiologically acceptable buffer solution. To stabilize the liposome complexes in vivo, a buffer solution containing albumin can also be used.

Then, when the suspension in which the phospholipid is dispersed in the buffer solution is passed through a filter with a pore diameter of 0.1 to 0.2 µm about 10 to 30 times, liposome complexes can be formed. The particle diameter of liposome complexes can be properly controlled by changing the type and concentration of the phospholipid, lipid and/or modified phospholipid used, the pore size of the filter, the material of the filter, the number of passages through the filter, and the like. If necessary, the formed liposomes can also be subjected to size fractionation to prepare liposomes having a desired diameter. For example, to anchor the liposomes in tumor tissue for a long period of time, the particle diameter thereof is preferably 20 to 250 nm, more preferably 50 to 200 nm.

The photothermal therapy and/or photodynamic therapy using the liposome complex of the present invention can be carried out, for example, by the intravenous or intratumoral administration of a physiological saline containing a prescribed concentration of the liposome complex of the present invention and, after a certain time, the irradiation of an affected area with light using an apparatus capable of irradiating with near-infrared light. The liposome complex concentration, the light irradiation time, and the like can be properly set considering a desired therapeutic effect.

The photothermal therapy and/or photodynamic therapy using the liposome complex of the present invention has a therapeutic effect on various tumors, for example, brain tumor, insulinoma, nasal cancer, oral cancer, kidney cancer, lung cancer, large bowel cancer, soft tissue sarcoma, and metastatic cancer (pleural metastasis, peritoneal metastasis).

When the liposome complex of the present invention is used in fluorescent imaging, the liposome complex of the present invention can be properly used alone or in the form of a liposome complex further containing a liposome membrane-constituting substance bonded to a near-infrared fluorescent dye as a constituent of the lipid bilayer membrane of the liposome complex or a liposome complex including a near-infrared fluorescent dye in the liposome. In some cases, the liposome complex of the present invention can also be properly used in combination with the liposome complex containing a liposome membrane-constituting substance bonded to a near-infrared fluorescent dye and/or a liposome including a near-infrared fluorescent dye in the liposome.

The present specification encompasses the contents of the specification and/or drawings of Japanese Patent Application No. 2011-223273 on which the priority of the present application is based.

EXAMPLES

The present invention is more specifically described below by way of Examples. However, the present invention is not intended to be limited thereto.

[Example 1] Synthesis of Indocyanine Green Dye ICG-8

ICG-8 as an indocyanine green dye of the present invention was synthesized according to the following scheme.

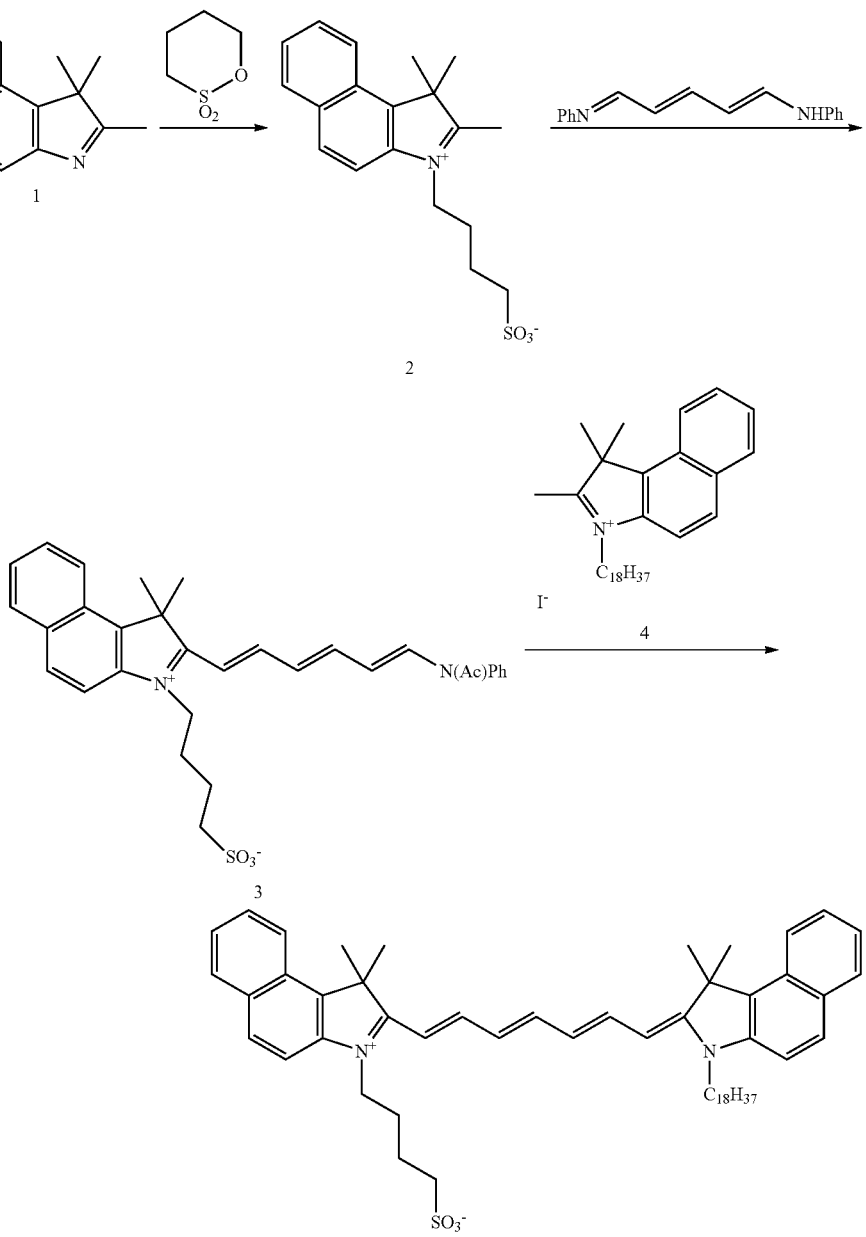

2,3,3-Trimethyl-1-(4-sulfobutyl)-4,5-benzoindolium Inner Salt (2)

In a 25-ml four necked flask were mixed 2,3,3-trimethyl-4,5-benzo-3H-indole (1) (3.1 g, 15 mmol) and 4-butane sultone (2.1 g, 15 mmol), and the container was purged with nitrogen. The mixture was stirred at 80° C. for 4 hours and then allowed to cool to room temperature, followed by adding acetone to precipitate the reaction mixture. After stirring for some time, the crystals were separated by filtration, washed with 10-ml acetone, and then air-dried to provide gray crystals (2) (1.17 g, 23%).

2-(6-acetanilide-1,3,5-hexatrienyl)-3,3-dimethyl-1-(sulfobutyl)-4,5-benzo[e]indolium inner salt (3)

In a 25-ml four necked flask were mixed the indolium salt (2) (1.04 g, 3.0 mmol) and glutaconaldehydedianil hydrochloride (0.94 g, 3.3 mmol), followed by stirring at 120° C. for 1 hour. The mixture was allowed to cool to room temperature and stirred for 1 hour, followed by separating crystals by filtration. The resultant crystals were suspended and washed in acetone, separated by filtration, and air-dried to provide a desired product (3) in a dark purple crystalline form (0.91 g, 58%).

1-Octadecyl-2,3,3-trimethyl-4,5-benzo[e]indolium Iodide (4)

In a 100-ml four necked flask were mixed 2,3,3-trimethyl-4,5-benzo-3H-indole (8.4 g, 40 mmol), 1-iodooetadecane (16.8 g, 44 mmol), and 2-butanone (30 ml), which was then stirred at 70° C. for 18 hours and allowed to cool to room temperature, followed by adding ethyl acetate (40 ml) and separating crystals by filtration. The resultant crystals were suspended and washed in ethyl acetate (twice), separated by filtration, and air-dried to provide a desired product (4) in a gray crystalline form (4.4 g, 19%).

4-(2-((1E,3E,5E,7E)-7-(1,1-dimethyl-3-octadecyl-1H-benzo[e]indol-2(3H)-ylidene)hepta-1,3,5-trienyl)-1,1-dimethyl-1H-benzo[e]indolium-3-yl)butane-1-sulfonic acid (5)

In a 50-ml three necked flask were mixed and dissolved the compound (3) (1.58 g, 3.0 mmol), the indolium salt (4) (1.77 g, 3.0 mmol), and 16 ml of pyridine, which was then reacted at 50° C. for 1 hour in a nitrogen atmosphere. After reaction, the reaction mixture was discharged into water (40 ml) and the precipitated crystals were separated by filtration. The resultant crude crystals were dissolved in ethyl acetate and then separated by filtration, and the resultant crystals were recrystallized from 40 ml of chloroform/ethyl acetate (1/1) to provide a desired product (5) in a dark green crystalline form (1.39 g, 53%).

The main molecular ion peak in LC-MS had a m/z of 867 (negative). The maximum absorption wavelength and the molar absorbance coefficient in ethanol were $\lambda$max=787 nm and $\epsilon$=2.30×10$^5$, respectively.

Example 2

(1) Fluorescence Spectrum
Dispersion of Liposome Including ICG (ICG
A chloroform/methanol (9:1, v/v) solution containing 10.0 mM of egg yolk-derived phosphatidylcholine and 3.2×10$^{-2}$ mM of ICG (Diagnogreen injection, Daiichi Sankyo) was prepared; 3 mL thereof was subjected to the distillation off of the solvent under reduced pressure; and 3 mL of a physiological saline was added to the formed thin membrane, which was then treated using a filter having a pore diameter of 0.22 μm to provide liposomes.

Dispersion of Liposome Having ICG-8 in Lipid Bilayer Membrane (LP-ICG-8)

A chloroform/methanol (9:1, v/v) solution containing 10.0 mM of egg yolk-derived phosphatidylcholine and 3.2×10$^{-2}$ mM of ICG-8 was prepared; 3 mL thereof was subjected to the distillation off of the solvent under reduced pressure; and 3 mL of a physiological saline was added to the formed thin membrane, which was then treated using a filter having a pore diameter of 0.22 μm to provide liposomes.

Figure 2:
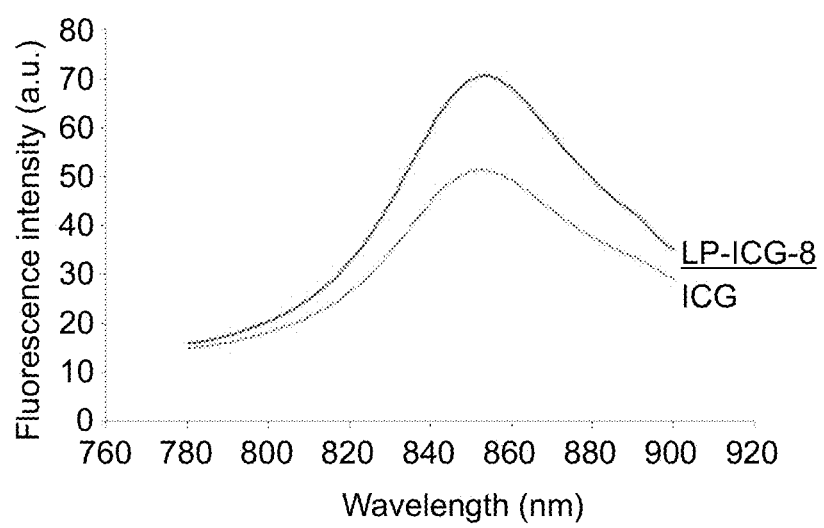
FIG. 2 is a graph showing the fluorescence properties of a dispersion of liposomes having ICG-8 in the lipid bilayer membrane (LP-ICG-8, hereinafter referred to the same) and a dispersion of liposomes including ICG (ICG).

When the above liposome dispersions were measured for fluorescence spectra (Jasco FP-6600), fluorescence spectra as shown in FIG. 2 were obtained at an excitation wavelength of 736 nm. The maximum fluorescence wavelength for ICG was 852 nm, and the maximum fluorescence wavelength for ICG-8 was 854 nm.

(2) Near-Infrared Camera Image after Intravenous Administration

ICG Aqueous Solution (ICG)

ICG was dissolved to 3.2 mM in pure water and diluted by 100-fold with a physiological saline.

Dispersion of Liposome Having ICG-8 in Lipid Bilayer Membrane (LP-ICG-8)

A chloroform/methanol (9:1, v/v) solution containing egg yolk-derived phosphatidylcholine (10.0 mM), cholesterol (1.0 mM), polyethylene glycol-modified phosphatidylethanolamine (PEG-PE) (5.0×10$^{-1}$ mM), and ICG-8 (3.2×10$^{-2}$ mM) was prepared; 5 mL thereof was evaporated under reduced pressure; 5 mL of a physiological saline was added to the formed thin membrane, which was then treated using a filter having a pore diameter of 0.22 μm; and the resultant was further treated using a filter having a pore diameter of 0.05 μm to provide liposomes.

Rat

Figure 3:
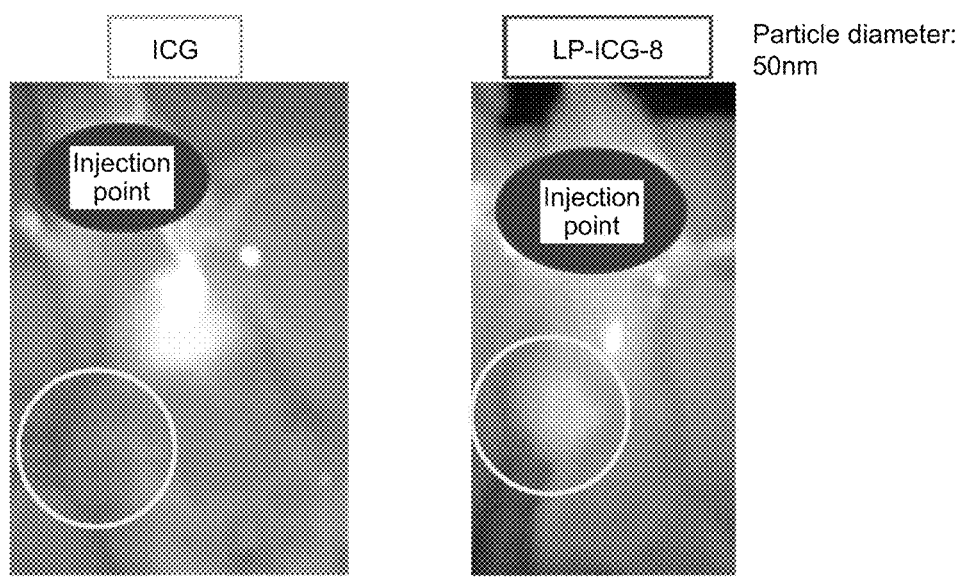
FIG. 3 is a pair of photographs each showing the results of fluorescently observing an affected area to which the LP-ICG-8 or ICG aqueous solution was intravenously administered.

F344/Jc1 34-36 weeks 9 L rats were used for the test. These are rats caused to bear cancer (glioma) under the skin using the brain tumor cells 9 L. The tumor tissue used had a tumor diameter of about 30 mm. After cutting the hair over the tumor location, 500 μL of the ICG aqueous solution or LP-ICG-8 was administered through the cervical vein. Fluorescent observation (Hyper Eye Medical System from Mizuho Corporation, excitation wavelength: 760 to 780 nm, fluorescence wavelength: >780 nm) was carried out 5 minutes after administration (FIG. 3). The distance between each rat and the camera head was 50 cm.

From FIG. 3, it is understood that whereas the use of the ICG aqueous solution (ICG) caused the dye diffusion and did not result in the accumulation of ICG in the tumor tissue, the use of LP-ICG-8 resulted in the accumulation of the liposomes including ICG-8 in the lipid bilayer membrane (LP-ICG-8) in the tumor tissue.

(3) Photodynamic Therapy/Photothermal Therapy

ICG Aqueous Solution (ICG) (2.5 mg/mL)

ICG was dissolved to 2.5 mg/mL in pure water.

Dispersion of Liposome Having ICG-8 in Lipid Bilayer Membrane (LP-ICG-8)

A chloroform/methanol (9:1, v/v) solution containing egg yolk-derived phosphatidylcholine (10.0 mM), cholesterol (1.0 mM), polyethylene glycol-modified phosphatidylethanolamine (PEG-PE) (5.0×10$^1$ mM), and ICG-8 (3.2×10$^{-2}$ mM) was prepared; 10 mL thereof was evaporated under reduced pressure; 10 mL of an ICG aqueous solution (2.5 mg/ml) was added to the formed thin membrane, which was then treated using a filter having a pore diameter of 0.22 μm; and the resultant was further treated using a filter having a pore diameter of 0.05 μm to provide liposomes.

Rat

Figure 4:
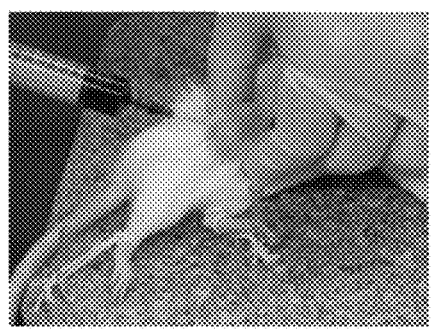
FIG. 4 is a pair of photographs each showing an overview of photodynamic therapy/photothermal therapy in a rat subcutaneous tumor model.
Figure 4:
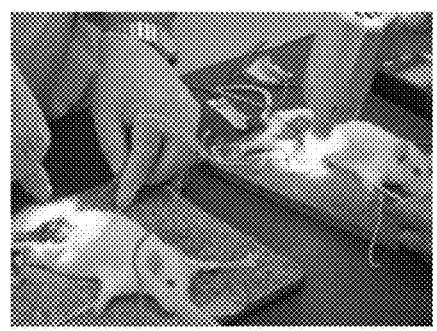
Figure 5:
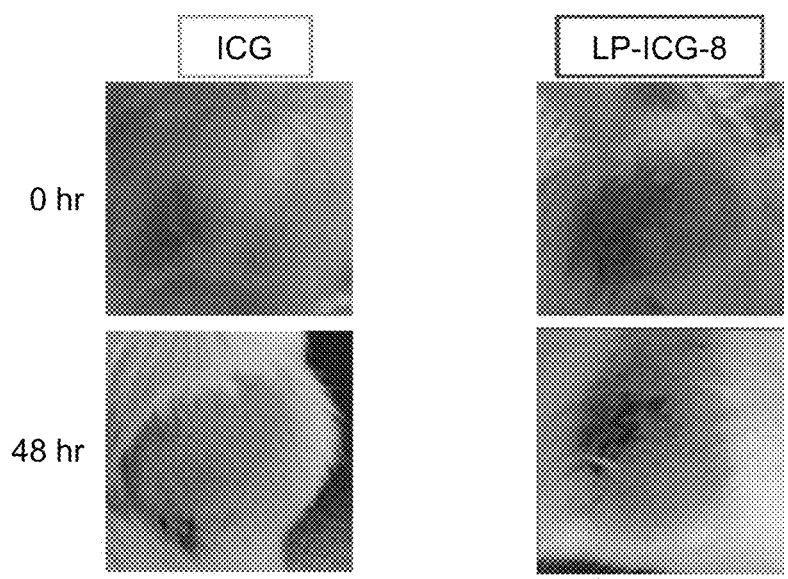
FIG. 5 is a set of photographs of tumor at immediately and 48 hours after the intratumoral administration of LP-ICG-8 or an ICG aqueous solution.
Figure 6:
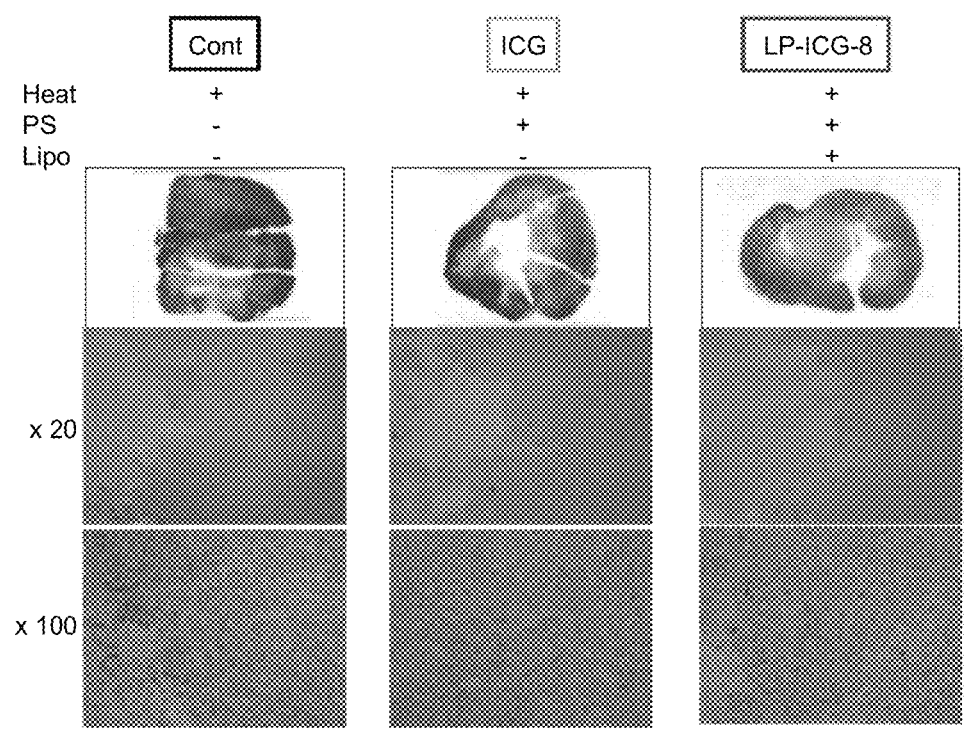
FIG. 6 is a series of photographs showing sections of the tumor tissues of FIG. 5 stained with hematoxylin-eosin (HE).

Tumor tissues having a tumor diameter of about 30 mm were used in F344/Jc1 34-36 weeks 9 L rats. After cutting the hair over the tumor location, 2 mL of each solution was intratumorally administered. Immediately after administration, light irradiation was performed at an output of 5 W and a wavelength of 600 to 1,600 nm for 20 minutes using a light irradiation apparatus (Tokyo Iken Co., Ltd., Super Lizer, Hyper 5000). Here, a thermometer was inserted into the tumor to measure the temperature of the skin surface, and when the temperature of the skin surface reached 45° C., ethanol was poured on the surface to prevent the burn of the skin. FIG. 4 shows an overview of photodynamic therapy/photothermal therapy in a rat subcutaneous tumor model; FIG. 5 shows a set of photographs of tumor at immediately and 48 hours after the intratumoral administration of LP-ICG-8 or an ICG aqueous solution; and FIG. 6 shows a photograph of each tissue section stained with hematoxylin-eosin (HE) by a method well-known to those of ordinary skill in the art. It is understood from FIG. 5 that the use of LP-ICG-8 produced significant tumor regression compared to the use of the ICG aqueous solution and, from FIG. 6 that the proportion of dead cells in all cells increased.

(4) Confirmation of Release Control of Included Agent by Near-Infrared Light

Figure 7:
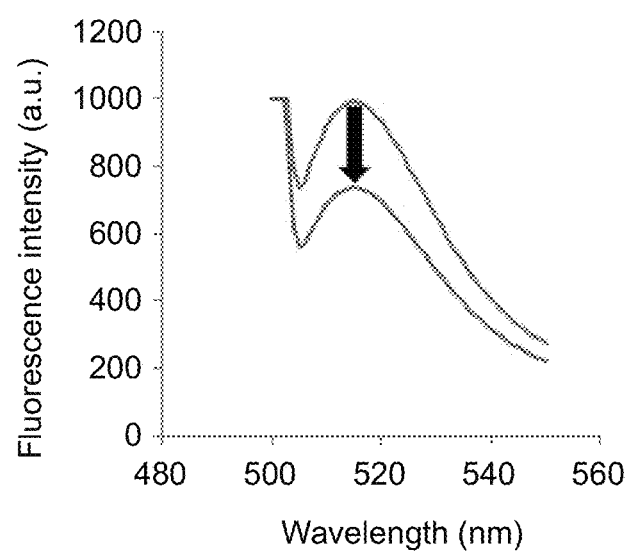
FIG. 7 is a graph accounting for the sustained release capacity of a drug of a liposome complex of the present invention.

A chloroform/methanol (9:1, v/v) solution containing ICG-8 ($3.2 \times 10^{-2}$ mM) and egg yolk-derived phosphatidylcholine (10.0 mM) was prepared, and 3 mL thereof was taken and subjected to the distillation off of the solvent under reduced pressure. To the formed thin membrane was added 1.5 mL of a fluorescein aqueous solution ($5.0 \times 10^{-2}$ mM) to swell the thin membrane, followed by adding 1.5 mL of a cobalt chloride aqueous solution (2.0 mM) as a fluorescence quencher. The fluorescence spectra were obtained at an excitation wavelength of 496 nm using a spectrophotofluorometer (Jasco FP-6600). Thereafter, the 1 minute irradiation with an 808 nm laser at about 1 W was repeated 5 times, and fluorescence spectra were similarly measured (FIG. 7). From FIG. 7, it is confirmed that since the fluorescence intensity after light irradiation was reduced, the fluorescein included in the liposome complex of the present invention was sustainedly released by the splitting of the liposome due to light irradiation.

(5) Release Control of Cisplatin (CDDP) by Near-Infrared Light

Aqueous Solution Containing ICG and Cisplatin (CDDP) (ICG+CDDP)

25 mg of ICG was dissolved to 3.2 mM in 9 ml of a physiological saline, which was then mixed with 1 ml of cisplatin (Randa Injection, Nippon Kayaku Co., Ltd.).

Aqueous Solution Containing Liposome Complex in which Cisplatin is Included in Liposome Having ICG-8 in Lipid Bilayer Membrane (LP-ICG-8_CDDP)

An aqueous solution was prepared in which 1 mL of CDDP was mixed with 9 mL of a physiological saline containing ICG-8 (3.2 mM). On the other hand, a chloroform/methanol (9:1, v/v) solution containing egg yolk-derived phosphatidylcholine (10.0 mM), cholesterol (1.0 mM), polyethylene glycol-modified phosphatidylethanolamine (PEG-PE) ($5.0 \times 10^{-1}$ mM), and ICG-8 ($3.2 \times 10^{-1}$ mM) was prepared, and 10 mL thereof was evaporated under reduced pressure to form a thin membrane. To the thin membrane was added 10 mL of an ICG solution containing cisplatin, and the resultant was treated using a filter having a pore diameter of 0.22 μm and then further treated using a filter having a pore diameter of 0.05 μm to provide liposome complexes.

Rat

Figure 8:
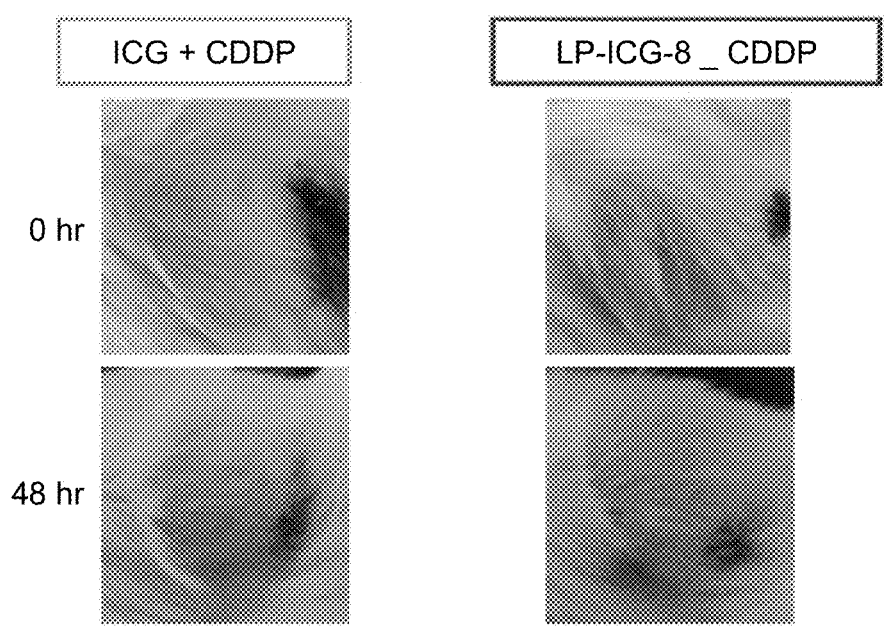
FIG. 8 is a set of photographs of tumor at immediately and 48 hours after the intratumoral administration of an aqueous solution containing ICG and cisplatin (CDDP) (ICG+CDDP) or an aqueous solution containing liposome complexes in each of which cisplatin is included in a liposome having ICG-8 in the lipid bilayer membrane (LP-ICG-8_CDDP).

Tumor tissues having a tumor diameter of about 30 mm were used in F344/Jc1 34-36 weeks 9 L rats. After cutting the hair over the tumor location, 2 mL of each solution was intratumorally administered. Immediately after administration, light irradiation was performed at an output of 5 W and a wavelength of 600 to 1,600 nm for 20 minutes using a light irradiation apparatus (Tokyo Iken Co., Ltd., Super Lizer, Hyper 5000). Here, a thermometer was inserted into the tumor to measure the temperature of the skin surface, and when the temperature of the skin surface reached 45° C., ethanol was poured on the surface to prevent the burn of the skin. FIG. 8 shows a pair of photographs of the tumors at immediately and 48 hours after intratumoral administration of ICG+CDDP or LP-ICG-8_CDDP, and FIG. 9 shows a series of photographs of tissue thin membranes thereof stained with HE.

Figure 9:
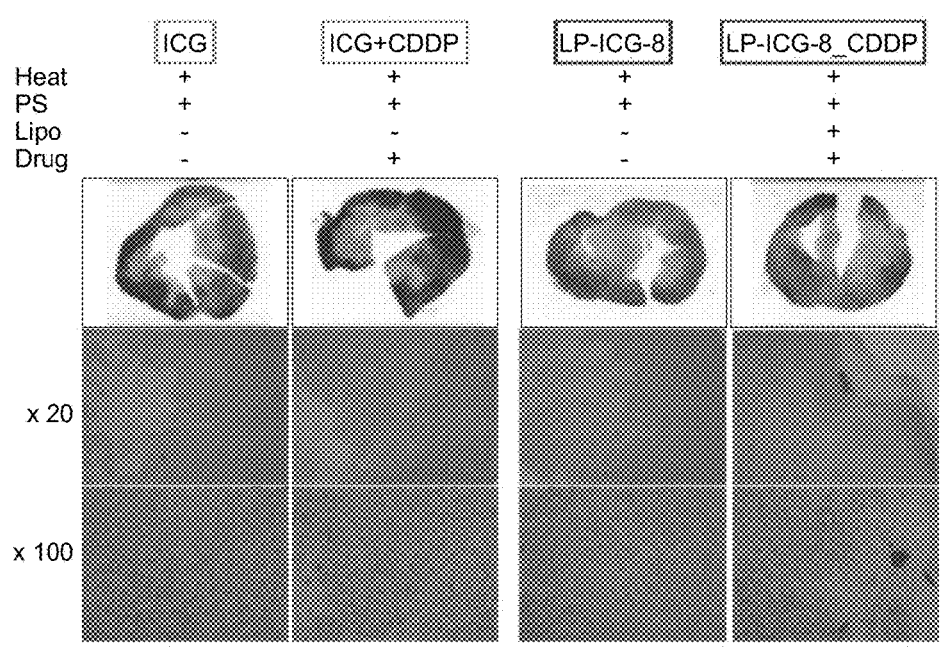
FIG. 9 is a series of photographs showing sections of the tumor tissues of FIG. 8 stained with HE.

It is understood from FIG. 8 that the use of LP-ICG-8_CDDP produced significant tumor regression compared to the use of ICG+CDDP and, from FIG. 9 that the proportion of dead cells in all cells increased.

[Example 3] Measurement of Singlet Oxygen from ICG-8

By the following measurement, it was confirmed that ICG-8 had a singlet oxygen-producing capacity. As a result, it turned out that ICG-8 had a capacity of producing singlet oxygen essential for performing photodynamic therapy.

The measurement conditions are as follows.

Excitation was carried out with a dye laser using an excitation wavelength of 690 nm, an average output of 20 mW, a repetition frequency of 30 Hz, a pulse width of about 10 nm, and DCM.

For detection, light was dispersed by a spectroscope (focal distance: 250 mm, grating: 600 L/mm) using a gated near-infrared image intensifier (NIR-PII) cooled at −80° C., followed by measurement for 200 microseconds from 30 microseconds after excitation.

Figure 10:
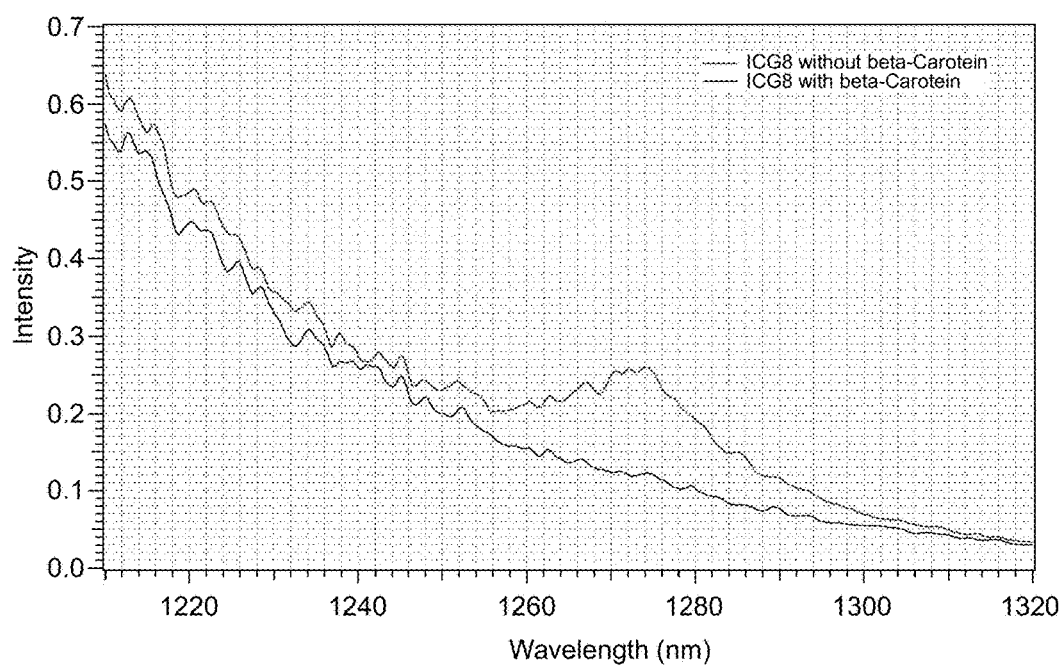
FIG. 10 is a graph showing the results of singlet oxygen measurement of ICG-8.

The results are shown in FIG. 10. In FIG. 10, the red line indicates the generation of singlet oxygen (1,270 nm) derived from ICG-8, and the blue line indicates singlet oxygen scavenging by β-carotene (concentration: 4 μM).

[Example 4] Synthesis of Indocyanine Green Dye ICG-11

ICG-11 as an indocyanine green dye of the present invention was synthesized according to the following scheme.

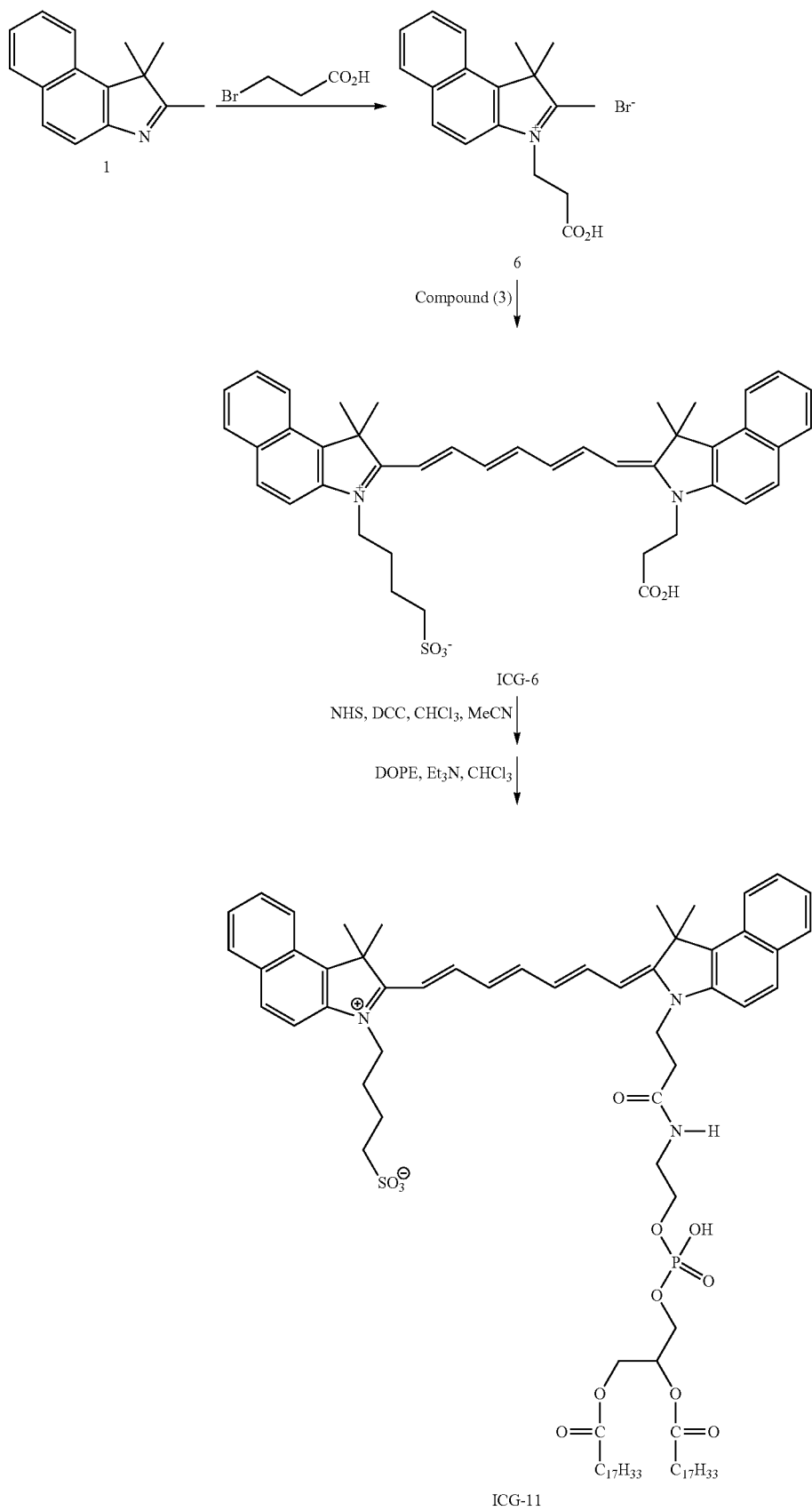

2,3,3-trimethyl-1-(2-carboxyethyl)-4,5-benzoindolium bromide (6)

In a 25-ml four necked flask were mixed 2,3,3-trimethyl-4,5-benzo-3H-indole (1) (2.3 g, 11 mmol), 3-bromo-1-propionic acid (1.5 g, 9.8 mmol), and acetonitrile (10 ml), which was then stirred at 65° C. for 16 hours, allowed to cool to room temperature, and discharged into ethyl acetate (50 ml). Crystals were separated by filtration, and the resultant crystals were suspended and washed in acetone, separated by filtration, and then air-dried to provide a desired product (6) in a gray crystalline form (1.68 g, 47%).

4-(2-((1E,3E,5E,7E)-7-(3-(2-carboxyethyl)-1,1-dimethyl-1H-benzo[e]indol-2(3H)-ylidene)hepta-1,3,5-trienyl)-1,1-dimethyl-1H-benzo[e]indolium-3-yl)butane-1-sulfonic acid (7) (ICG-6)

In a 25-ml four necked flask were mixed the compound (6) (0.55 g, 1.5 mmol), the compound (3) described in Example 1 (0.80 g, 1.5 mmol), and pyridine (8 ml), which was then stirred at 50° C. for 45 minutes and allowed to cool to room temperature. The reaction solution was concentrated under reduced pressure; water (20 ml) was added to the residue, which was then stirred; and then 10% hydrochloric acid was added in small portions before stirring for some time (pH 3 to 4). Crystals were separated by filtration and air-dried to provide a crude product (1.12 g). To the resultant crystals was added 20 ml of methanol/chloroform (5/1), which was then heat stirred and allowed to cool, followed by separating crystals by filtration. The resultant crystals were recrystallized from methanol/chloroform, separated by filtration, and air-dried to provide ICG-6 in a dark green crystalline form (0.38 g, 37%).

The main molecular ion peak in LC-MS had a m/z of 687 (negative). The maximum absorption wavelength and the molar absorbance coefficient in ethanol were respectively $\lambda max=786$ nm and $\epsilon=1.86\times10^5$.

4-(2-((1E,3E,5E,7E)-7-(3-(2-(1,2-dioleoyl-sn-glycero-3-phosphoethanolaminocarbonyl)ethyl)-1,1-dimethyl-1H-benzo[e]indol-2(3H)-ylidene)hepta-1,3,5-trienyl)-1,1-dimethyl-1H-benzo[e]indolium-3-yl)butane-1-sulfonic acid (8) (ICG-11)

In a 25-ml four necked flask were charged ICG-6 (7) (0.5 g, 0.73 mmol), N-hydroxysuccinimide (NHS) (0.17 g, 1.5 mmol), acetonitrile (3 mL), and chloroform (10 mL), and the container was purged with nitrogen. A mixture of N,N'-dicyclohexylcarbodiimide (DCC) (0.30 g, 1.5 mmol) and chloroform (2 mL) was dropwise added over 10 minutes thereto while keeping at 2° C. The resultant was slowly heated up to room temperature and stirred for 30 minutes, followed by filtering the reaction solution. The filtrate was concentrated under reduced pressure while keeping at 25° C. or lower; the residue was loosened with ethyl acetate; and crystals were collected by filtration and suspended and washed in acetone to provide crude crystals of an ICG-11 precursor (N-hydroxysuccinimidyl ester) (0.66 g). Subsequently, the resultant crystals (0.66 g, ca. 0.73 g) and chloroform (10 mL) were charged in a 25-ml four necked flask, and thereto was dropwise added a mixture of 1,2-dioleoyl-sn-glycero-3-phosphoethanolamine (DOPE; COATSOME ME-8181 from NOF Corporation) (0.54 g, 0.73 mmol), triethylamine (0.10 g, 1.0 mmol), and chloroform (5 mL) over 20 minutes in a nitrogen atmosphere. The resultant was stirred for 2.5 hours at room temperature; the reaction solution was filtered; the filtrate was concentrated; and the residue was purified using a flash column (SiO$_2$, CHCl$_3$/MeOH=4/1 to 3/1) to provide ICG-11 (8) (0.37 g, 36%).

Example 5

(1) Fluorescence Spectral Characteristic of ICG-11

The physical properties of ICG-11 were examined in aqueous solutions different in polarity in comparison with ICG. As a result, ICG-11 was found to emit fluorescence stronger than that of ICG.

(a) Comparison in Methanol as Polar Solvent

ICG-11 was found to emit 1.5-fold strong fluorescence compared to ICG.

(b) Comparison in Chloroform as Non-Polar Solvent

ICG-11 was found to emit sufficiently strong fluorescence in contrast to ICG not emitting fluorescence.

Figure 11:
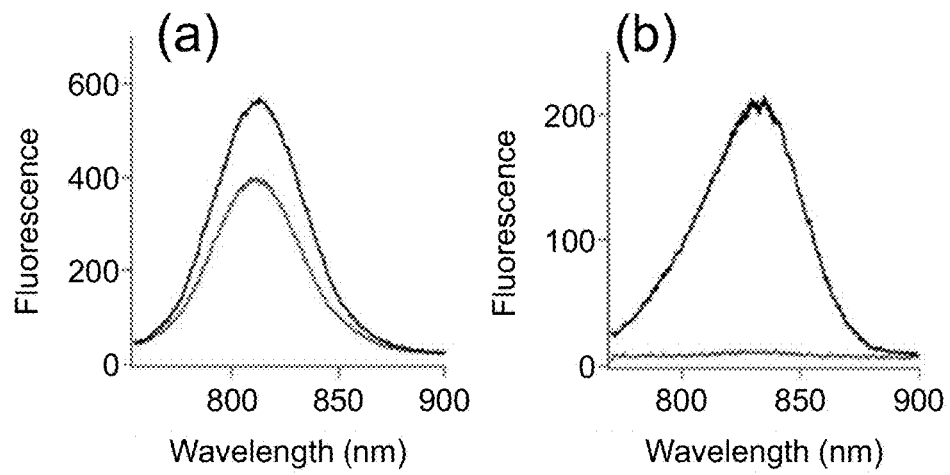
FIG. 11 is a pair of graphs showing the results of comparing the fluorescence spectral characteristics of ICG-11 with those of ICG in (a) methanol as a polar solvent and (b) chloroform as a nonpolar solvent.

The results are shown in FIG. 11. In FIG. 11, the black and red lines indicate the results for ICG-11 (concentration: 1 μM) and ICG (concentration: 1 μM), respectively.

(2) Measurement of Singlet Oxygen from ICG-11

By the following measurement, it was confirmed that ICG-11 had a singlet oxygen-producing capacity. As a result, it turned out that ICG-11 had a capacity of producing singlet oxygen essential for performing photodynamic therapy.

The measurement conditions were as follows.

Excitation was carried out with a dye laser using an excitation wavelength of 690 nm, an average output of 20 mW, a repetition frequency of 30 Hz, a pulse width of about 10 nm, and DCM.

For detection, light was dispersed by a spectroscope (focal distance: 250 mm, grating: 600 L/mm) using a gated near-infrared image intensifier (NIR-PII) cooled at −80° C., followed by measurement for 200 microseconds from 30 microseconds after excitation.

Figure 12:
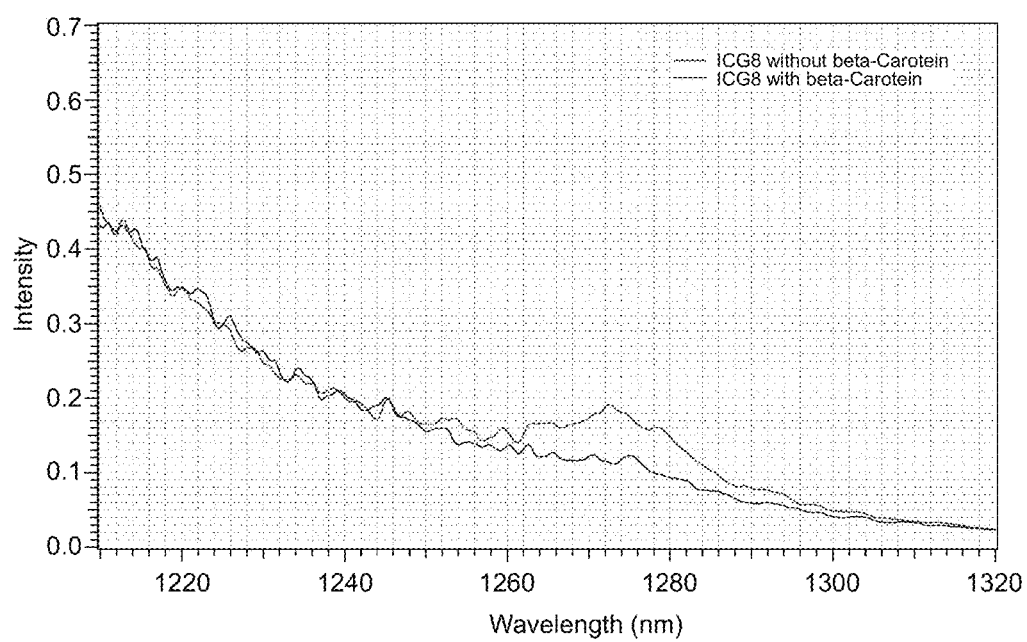
FIG. 12 is a graph showing the results of singlet oxygen measurement of ICG-11.

The results are shown in FIG. 12. In FIG. 12, the red line indicates the generation of singlet oxygen (1,270 nm) derived from ICG-11, and the blue line indicates singlet oxygen scavenging by β-carotene (concentration: 6 μM).

(3) Heat Generating Capacity of ICG-11

The heat generating capacity of ICG was measured using the following conditions. As a result, it turned out that ICG-11 had a heat-generating capacity (increasing the tissue temperature from 37° C. to 43° C.) essential for performing hyperthermia.

The measurement conditions were as follows.

Excitation was carried out at an excitation wavelength of 808 nm and an output of 0.5 W/m$^2$. The temperature was measured at 1-second intervals.

Figure 13:
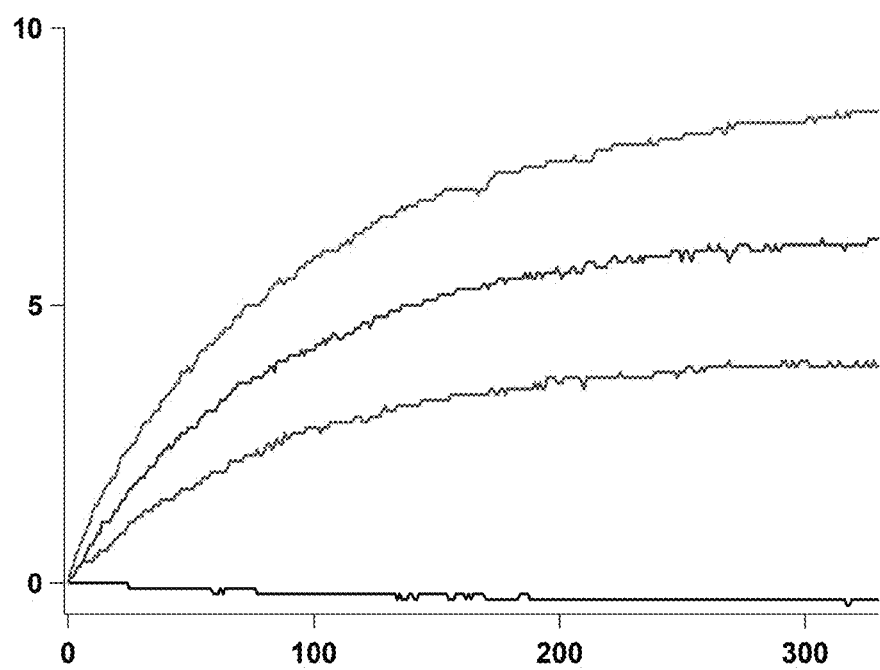
FIG. 13 is a graph showing the results of the heat generating capacity measurement of ICG-11.

The results are shown in FIG. 13. In FIG. 13, the black, red, blue, and green lines indicate the results when the concentration of ICG-11 was 0 μM, 1 μM, 2 μM, and 4 μM, respectively.

(4) Method for Preparing Dispersion of Liposome Having ICG-11 in Lipid Bilayer Membrane (LP-ICG-11)

(4-a) Forming Method

The amount of ICG-11 loadable in the liposome was examined by changing the mixing ratio between ICG-11 and dioleoylphosphatidylcholine (DOPC) as the main component of the lipid bilayer membrane. For comparison, the amount of loadable ICG was examined.

In chloroform/methanol (9:1, v/v) solution were dissolved DOPC (10 mM), cholesterol (5 mM), polyethylene glycol-modified phosphatidylethanolamine (PEG-PE, 0.5 mM), and ICG-11 (0 to 5 mM) or ICG (0 to 0.5 mM); a portion of the resultant solution was dried under reduced pressure; and a physiological saline was added to the formed thin membrane, which was then treated using a filter having a pore diameter of 100 nm to provide a liposome dispersion.

(4-b) Loading Amount

The amount of incorporation of ICG-11 into the lipid bilayer membrane when it formed a liposome was measured using the following conditions.

Figure 14:
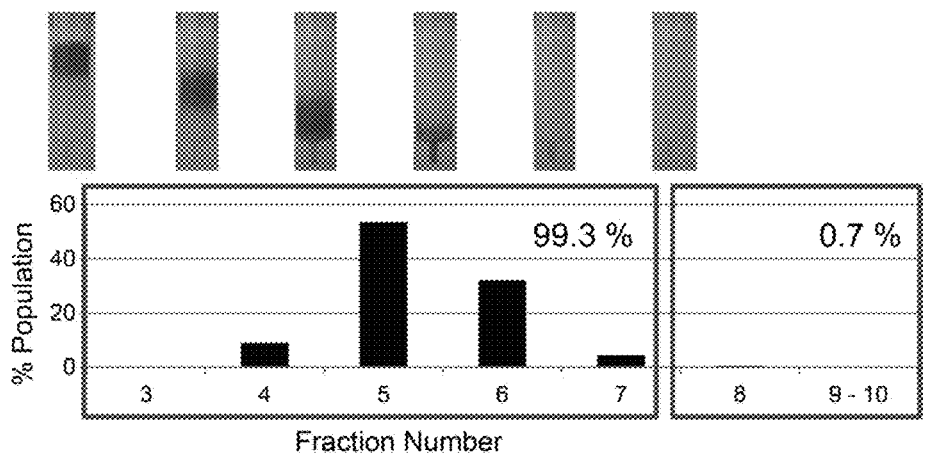
FIG. 14 is a series of drawings showing the result of measuring the amount of ICG-11 and ICG loaded in liposomes.
Figure 14:
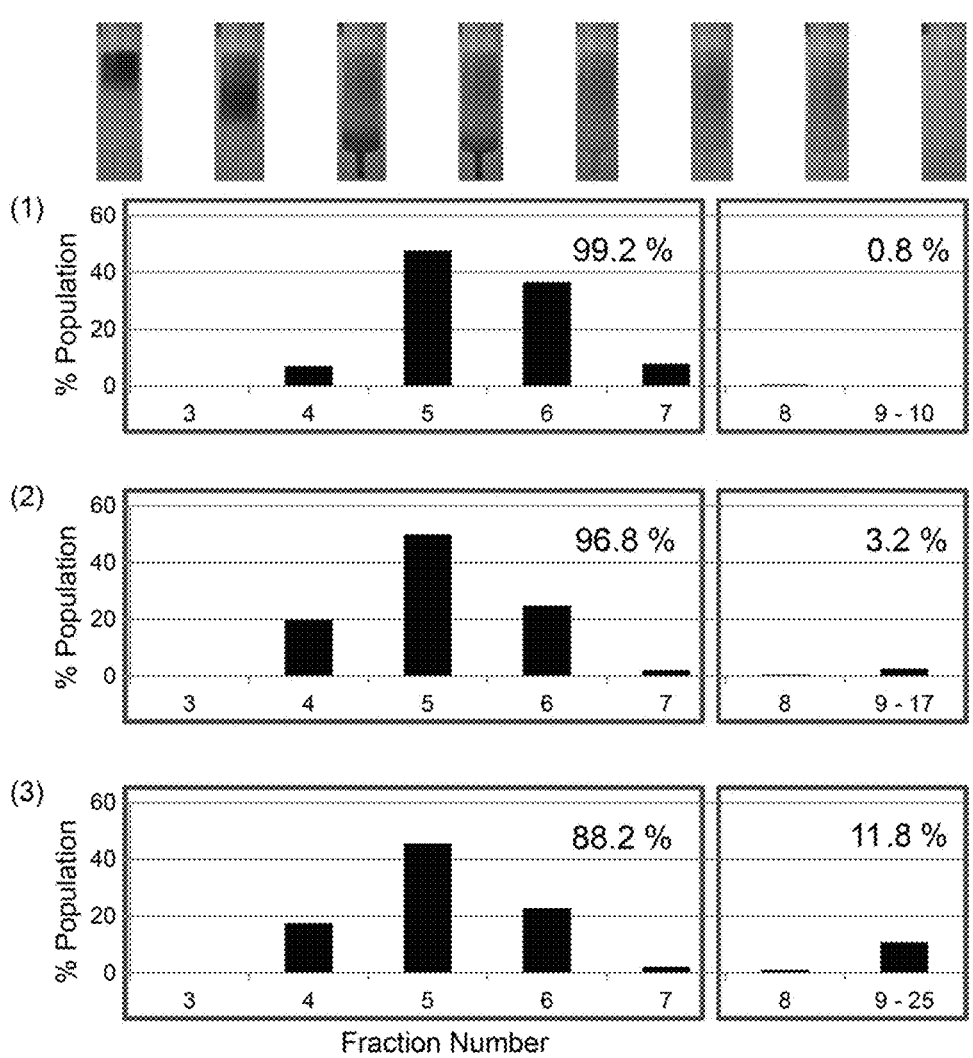

Liposomes into which ICG-11 or ICG was incorporated and ICG-11 or ICG released into a liposome dispersion without being incorporated into the lipid bilayer membrane were separated and determined using a gel filtration column (PD-10 from GE) (FIG. 14).

As a result, ICG-11 was found to be capable of being incorporated until the ratio of ICG-11 to DOPC as the main component of the lipid bilayer membrane reaches up to 1:2 (FIG. 14a).

In contrast, ICG was found to be capable of being incorporated until the ratio of ICG to DOPC as the main component of the lipid bilayer membrane reaches up to 1:100 (FIG. 14b-(1)).

When liposomes were formed at a ratio of ICG:DOPC of 1:40 (FIG. 14b-(2)) or 1:20 (FIG. 14b-(3)), it was confirmed that ICG not incorporated into the lipid bilayer membrane increased in the dispersion.

(4-c) Particle Diameter

The relation between the amount of incorporation of ICG-11 into the lipid bilayer membrane and the particle diameter when it formed a liposome was measured using the following conditions.

ICG-11 was incorporated into liposomes at various ratios, and the particle diameter for each content (0.0, 0.5, 1.0, 5.0, or 10.0%) in the lipid bilayer membrane was measured using a dynamic light scattering measurement apparatus SZ-100.

Figure 15:
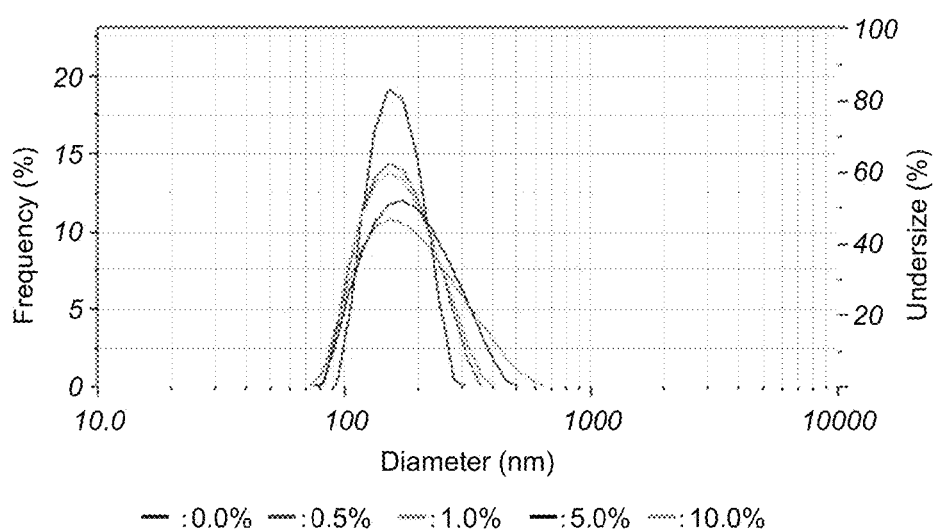
FIG. 15 is a graph showing particle diameter distribution due to the difference in the ICG-11 content.

As a result, with an increase in the content of ICG-11, the distribution of particle diameters of the liposomes (FIG. 15) became broader as well as the arithmetic mean diameter thereof (Table 1) increasing; however, the values in both cases were confirmed to be in the range satisfying the conditions for the EPR effect.

TABLE 1

Arithmetic Mean Diameter of Liposome due to Difference in ICG-11 Content

| Surface Agent Content | Arithmetic Mean Diameter (nm) |
|---|---|
| 0.0% | 154.9 |
| 0.5% | 160.2 |
| 1.0% | 163.0 |
| 5.0% | 182.9 |
| 10.0% | 191.2 |

(4-d) Zeta Potential

The relation between the amount of incorporation of ICG-11 into the lipid bilayer membrane and the zeta potential when it formed a liposome was measured using the following conditions.

ICG-11 was incorporated into liposomes at various ratios, and the zeta potential for each content (0.0, 3.1, 6.3, 12.5, or 25.0%) in the lipid bilayer membrane was measured using the dynamic light scattering measurement apparatus SZ-100.

As a result, with an increase in the content of ICG-11, the absolute values of zeta potentials of the liposomes increased (Table 2), confirming the formation of stable liposomes.

TABLE 2

Zeta Potential of Liposome due to Difference in ICG-11 Content

| Surface Agent Content | Zeta Potential (mV) |
|---|---|
| 0.0% | −3 |
| 3.1% | −43 |
| 6.3% | −47 |
| 12.5% | −55 |
| 25.0% | −70 |

(5) UV Spectral Characteristic of Dispersion of Liposome Having ICG-11 in Lipid Bilayer Membrane (LP-ICG-11)

ICG-11 was examined for the UV spectral characteristics of a dispersion of liposomes in which it was incorporated into the lipid bilayer membrane (LP-ICG-11), in comparison with ICG. As a result, it turned out that ICG-11 was incorporated into the lipid bilayer membrane to shift the absorption spectrum thereof to the side of a wavelength longer than for ICG.

Figure 16:
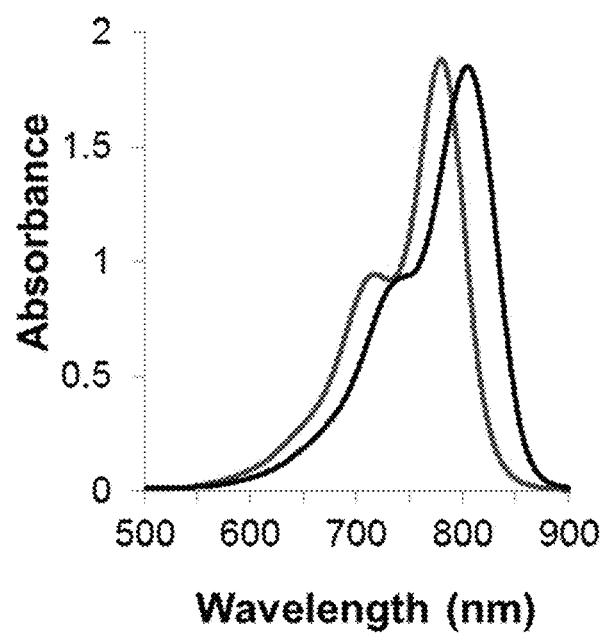
FIG. 16 is a graph showing the UV spectral characteristics of a dispersion of liposomes having ICG-11 in the lipid bilayer membrane.

The results are shown in FIG. 16. In FIG. 16, the black and red lines indicate the measurement results for LP-ICG-11 (concentration: 10 μM) and ICG (concentration: 10 μM), respectively.

(6) Fluorescence Spectral Characteristic of Dispersion of Liposome Having ICG-11 in Lipid Bilayer Membrane (LP-ICG-11)

ICG-11 was examined for the fluorescence spectral characteristics of a dispersion of liposomes in which it was incorporated into the lipid bilayer membrane (LP-ICG-11), in comparison with ICG. As a result, it was observed that ICG-11 was incorporated into the lipid bilayer membrane to shift the fluorescence spectrum thereof to the side of a wavelength longer than for ICG as well as increasing the emission intensity.

Figure 17:
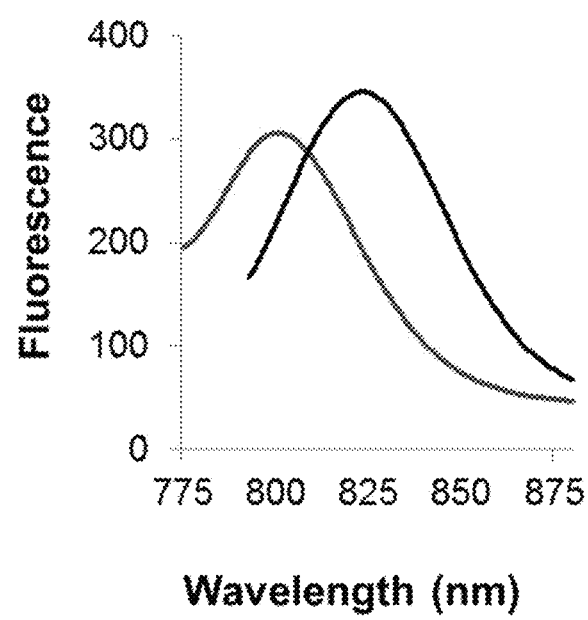
FIG. 17 is a graph showing the fluorescence spectral characteristics of a dispersion of liposomes having ICG-11 in the lipid bilayer membrane.

The results are shown in FIG. 17. In FIG. 17, the black and red lines indicate the measurement results for LP-ICG-11 (concentration: 1 μM) and ICG (concentration: 1 μM), respectively.

(7) Heat-Generating Capacity of Dispersion of Liposome Having ICG-11 in Lipid Bilayer Membrane (LP-ICG-11)

The heat-generating capacity of LP-ICG-11 was measured using the following conditions. As a result, LP-ICG-11 was found to have a heat-generating capacity (increasing the tissue temperature from 37° C. to 43° C.) essential for performing hyperthermia.

(7-a) In Vitro

Measurement Condition

A test tube was filled with 1.5 mL of the solution, and excitation was performed at an excitation wavelength of 808 nm and an output of 0.5 W/m$^2$. The temperature was measured at 1-second intervals.

Figure 18:
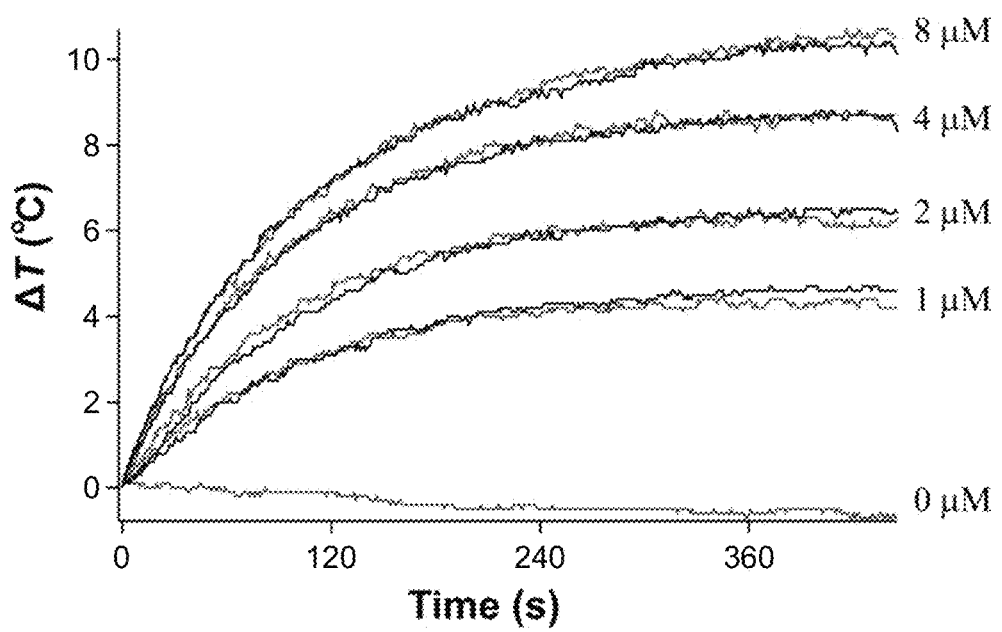
FIG. 18 is a graph showing the results of measuring the heat generating capacity of LP-ICG-11 in vitro.

The results are shown in FIG. 18. In FIG. 18, the black, red, and blue lines indicate the measurement results for LP-ICG-11, ICG, and control (physiological saline), respectively.

(7-b) In Vivo

Measurement Condition

LP-ICG-11 or a physiological saline was administered through the tail vein of nude mice, and 3 days thereafter, excitation was performed at an excitation wavelength of 800 nm and an output of 0.22 W/m$^2$. The temperature was measured at 1-second intervals.

Figure 19:
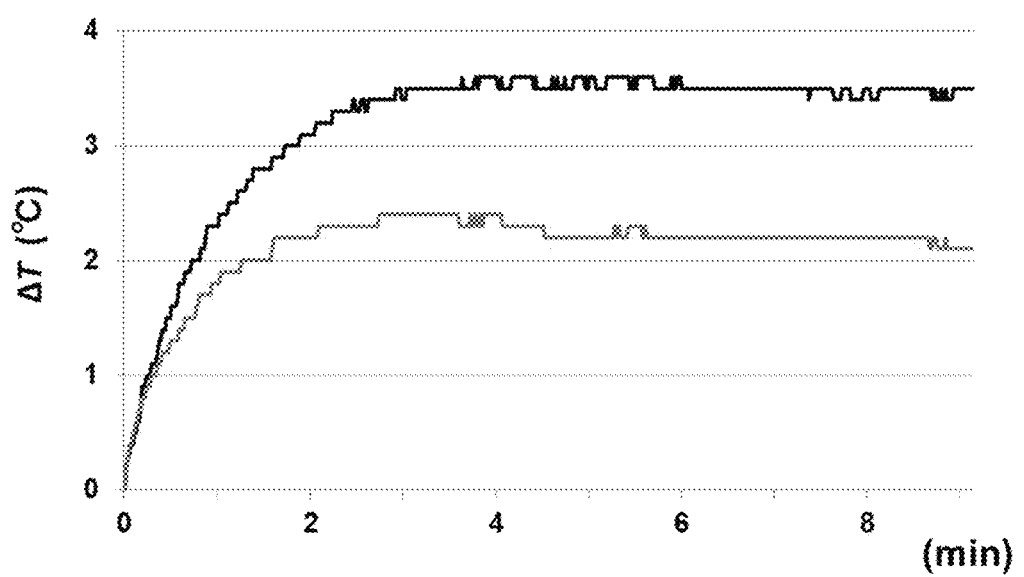
FIG. 19 is a graph showing the results of measuring the heat generating capacity of LP-ICG-11 in vivo.

The results are shown in FIG. 19. In FIG. 19, the black and blue lines indicate the measurement results for LP-ICG-11 and control (physiological saline), respectively.

(8) Change in Body Distribution of Dispersion of Liposome Having ICG-11 in Lipid Bilayer Membrane (LP-ICG-11)
(8-a) Comparison Between Tumor and Body Surface The tumor-specific accumulation capacity of LP-ICG-11 was examined by comparing it with the accumulation capacity thereof in the body surface according to time. LP-ICG-11 was administered through the tail vein of nude mice, and the condition of distribution thereof was measured 1 hour, 1 day, 2 days, and 3 days after administration. As a result, specific accumulation in the tumor was observed from 1 day after administration, and the specific accumulation became more marked as time passed.

Figure 20:
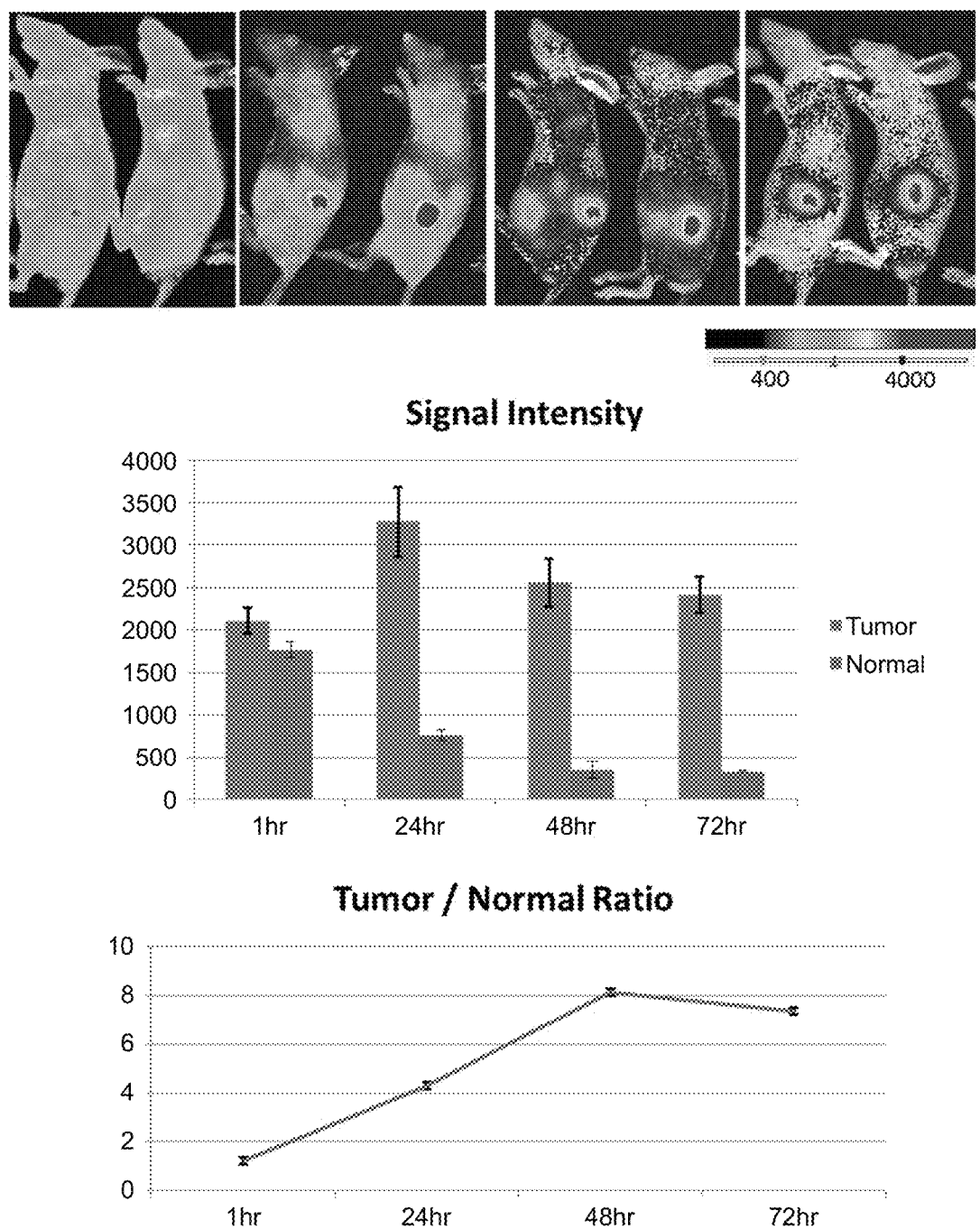
FIG. 20 is a series of drawings showing the results of comparing a change in the body distribution of LP-ICG-11 between tumor and the body surface.

The results are shown in FIG. 20.

(8-b) Comparison Between Tumor and Each Organ

The tumor-specific accumulation capacity of LP-ICG-11 was examined by comparing it with the accumulation capacity thereof in other organs according to time. LP-ICG-11 was administered through the tail vein of nude mice, and the condition of distribution thereof was measured 1 hour, 1 day, 2 days, and 3 days after administration. As a result, specific accumulation in the tumor was observed from 1 day after administration, and the specific accumulation became more marked as time passed.

Figure 21:
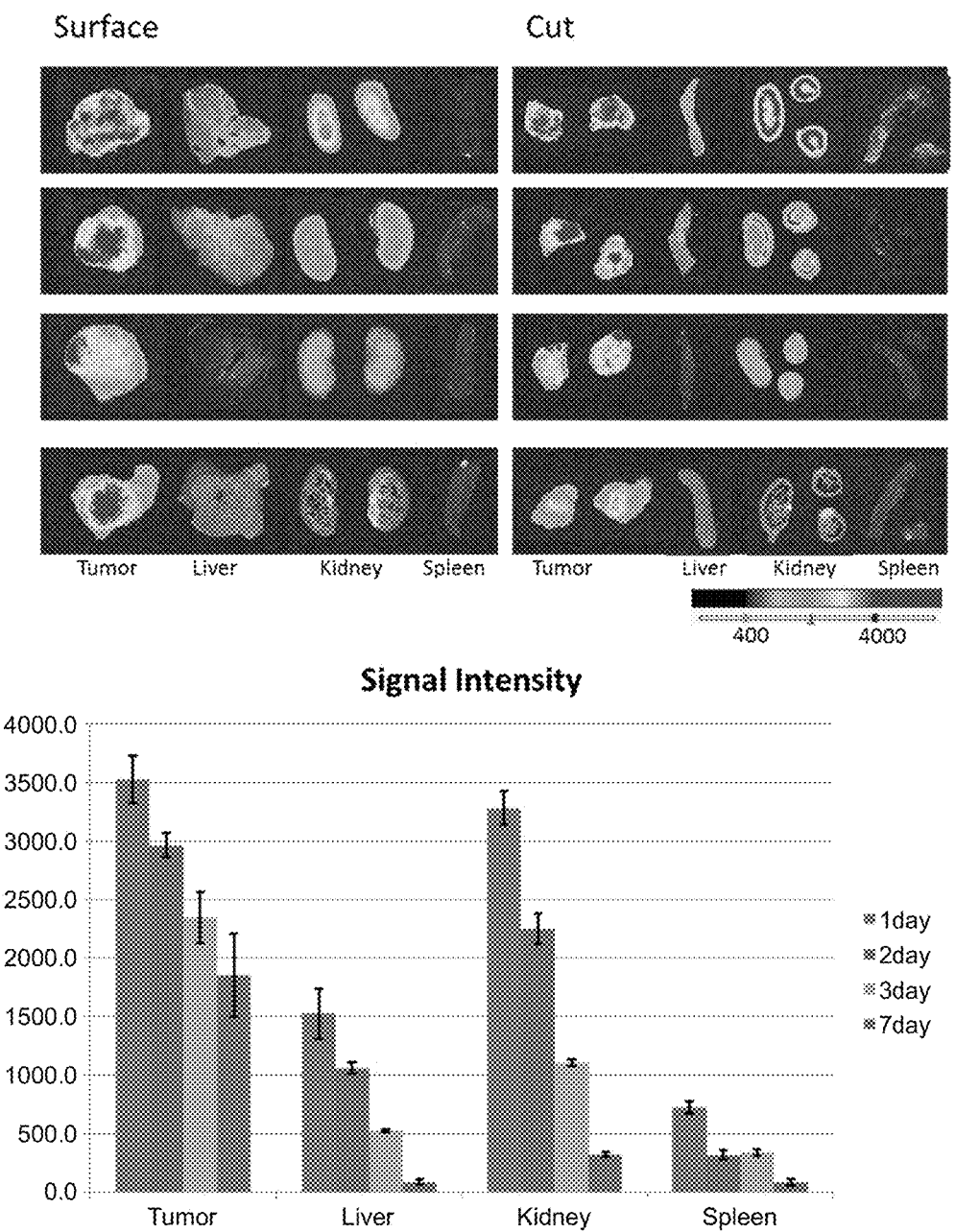
FIG. 21 is a series of drawings showing the results of comparing a change in the body distribution of LP-ICG-11 between tumor and each organ.

The results are shown in FIG. 21.

(9) Therapeutic Effect of Dispersion of Liposome Having ICG-11 in Lipid Bilayer Membrane (LP-ICG-11)
(9-a) Rat; Brain Tumor The anti-cancer effect of LP-ICG-11 was examined in a rat (F344/Jc1) brain tumor model.

Treatment Method

LP-ICG-11 (containing 17.5 mg) was administered through the tail vein, and treatment was carried out using the following protocol.

Figure 22:
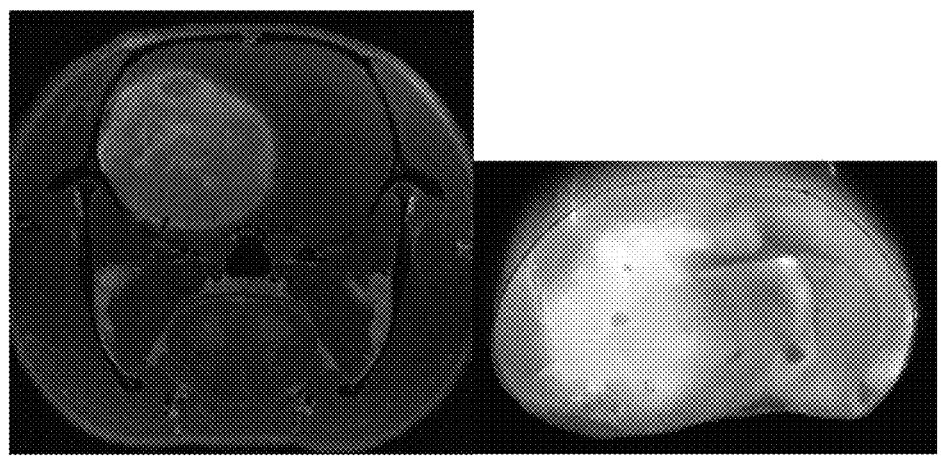
FIG. 22 is a pair of photographs showing an MRI image of brain tumor (left) and a near-infrared fluorescence image of brain tumor (right).

Treatment Regimen Featuring One Course Per 2 Weeks
Day 1 (Monday); LP-ICG-11 administration
Day 1 (Monday); near-infrared light irradiation (800 nm LED light, 0.25 W/m², 20 minutes)
Day 2 (Tuesday); near-infrared light irradiation (800 nm LED light, 0.25 W/m², 20 minutes)
Day 3 (Wednesday); near-infrared light irradiation (800 nm LED light, 0.25 W/m², 20 minutes)
Day 5 (Friday); tumor measurement by MRI
Day 12 (Friday); tumor measurement by MRI Course of Treatment The brains of rats after the end of treatment were removed, and the specific accumulation of LP-ICG-11 in tumor tissue was checked using a near-infrared fluorescence observing apparatus. As a result, as shown in FIG. 22, LP-ICG-11 could be confirmed to accumulate only in the tumor tissue.

Treatment Result

Figure 23:
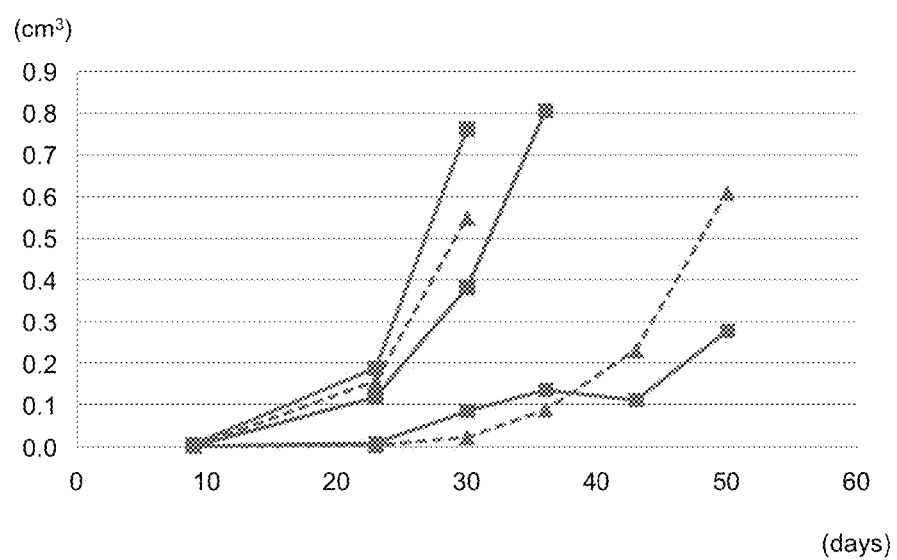
FIG. 23 is a graph showing changes in the brain tumor volume after treatment.

The anti-cancer effect of LP-ICG-11 prolonged, by 7 weeks or more, the life of rats, which otherwise generally resulted in death in 4 weeks (FIG. 23). An effective therapeutic effect, but not a complete cure, was produced. In FIG. 23, the blue, red, and purple lines indicate control, near-infrared light irradiation, and LP-ICG-11/near-infrared light irradiation, respectively.

(9-b) Cat; Apocrine Adenocarcinoma and Lung and Colon Metastases

The anti-cancer effect of LP-ICG-11 was examined in a cat with apocrine adenocarcinoma/lung and colon metastases (cat species: crossbred, age: 18 years old).

History of Disorder

Developed were concomitant lung and colon metastases whose primary tumor was apocrine adenocarcinoma.

Treatment Method

LP-ICG-11 (containing 17.5 mg) was administered by intravenous injection, and treatment was carried out using the following protocol.

Figure 24:
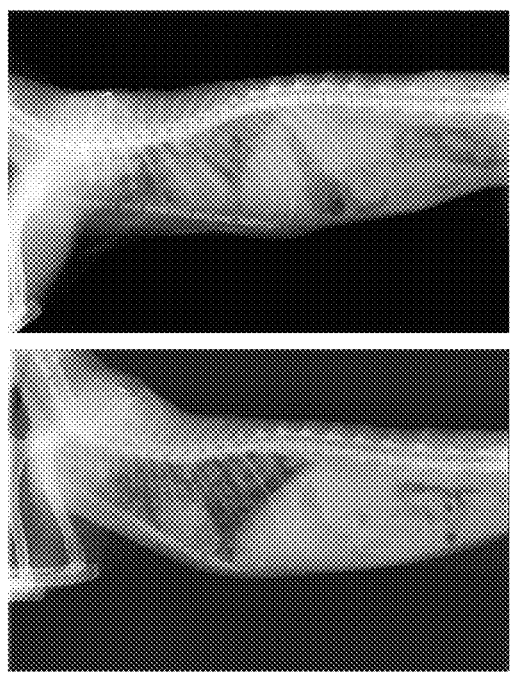
FIG. 24 is a pair of X-ray pictures (upper: before treatment, lower: at the 2nd course) of a cat (apocrine adenocarcinoma, and lung and colon metastases).

Treatment Regimen Featuring One Course Per 2 Weeks
Day 1 (Monday); LP-ICG-11 administration
Day 1 (Monday); near-infrared light irradiation (Super Lizer, Hyper 5000 from Tokyo Iken Co., Ltd.)
Day 3 (Wednesday); near-infrared light irradiation (Super Lizer, Hyper 5000 from Tokyo Iken Co., Ltd.)
Day 5 (Friday); near-infrared light irradiation (Super Lizer, Hyper 5000 from Tokyo Iken Co., Ltd.)
Day 8 (Monday); near-infrared light irradiation (Super Lizer, Hyper 5000 from Tokyo Iken Co., Ltd.)
Day 10 (Wednesday); near-infrared light irradiation (Super Lizer, Hyper 5000 from Tokyo Iken Co., Ltd.)
Day 12 (Friday); near-infrared light irradiation (Super Lizer, Hyper 5000 from Tokyo Iken Co., Ltd.) Course of Treatment (FIG. 24)

Course 1; A state of remission was kept (SD; Stable Disease). The bloody stool amount was decreased.
Course 2; The partial disappearance of lung metastatic tumor was confirmed (FIG. 24, lower).
Course 3; A state of remission was kept (SD; Stable Disease).
Course 4; A state of remission was kept. Died at home.

Treatment Result

The anti-cancer effect of LP-ICG-11 was confirmed to eliminate a part of lung metastatic tumor as well as decreasing bleeding from the colon, and found to enable a state of remission to be kept over a long period of time.

The results suggesting efficacy in palliative treatment were obtained.

(9-c) Dog; Circumanal Adenocarcinoma/Lymph Node Metastasis

The anti-cancer effect of LP-ICG-11 was examined in a dog with circumanal adenocarcinoma/lymph node metastasis (dog species: papillon, age: 11 years old).

History of Disorder

Developed was concomitant sublumbar lymph node metastasis whose primary tumor was circumanal adenocarcinoma.

Treatment Method

LP-ICG-11 (containing 17.5 mg) was administered by intravenous injection, and treatment was carried out using the following protocol.

Figure 25:
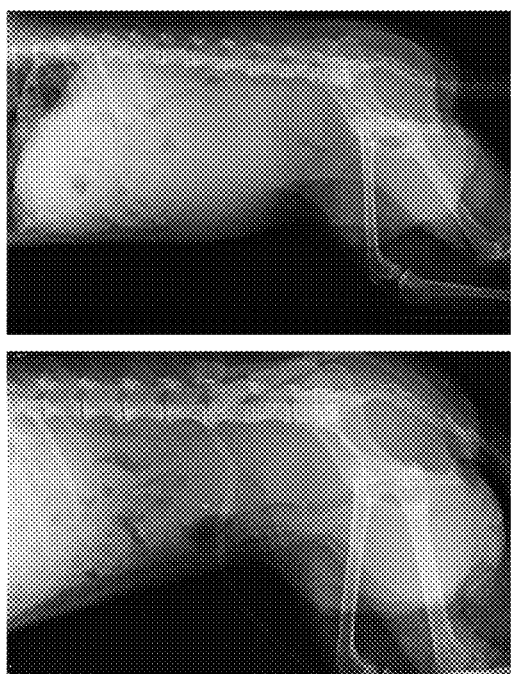
FIG. 25 is a pair of X-ray pictures (upper: before treatment, lower: on the 8th day of the 1st course) of a dog (perianal gland cancer/lymph node metastasis).
Figure 26:
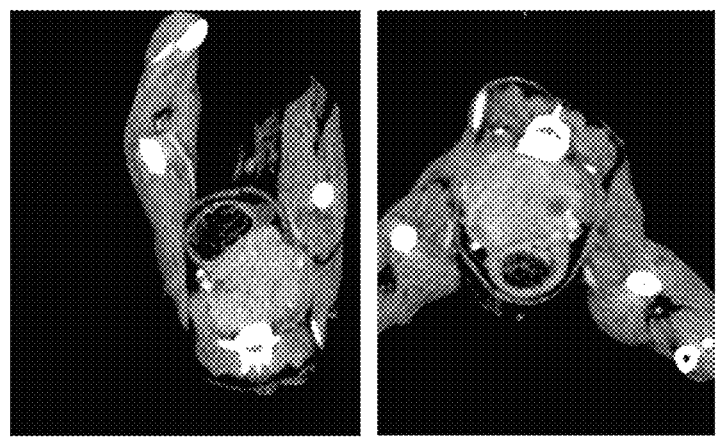
FIG. 26 is a pair of X-ray pictures (left: before treatment, lower: at 2 weeks after the end of the 2nd course) of a dog (perianal gland cancer/lymph node metastasis).
Figure 27:
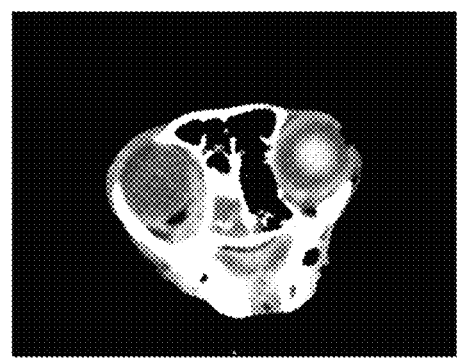
FIG. 27 is a CT photograph (before treatment) of a cat (intranasal lymphoma).
Figure 28:
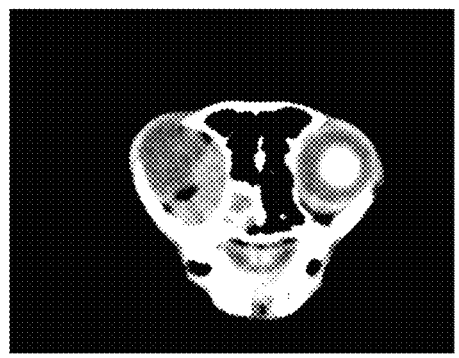
FIG. 28 is a CT photograph (on the 7th day of the 1st course) of a cat (intranasal lymphoma).
Figure 29:
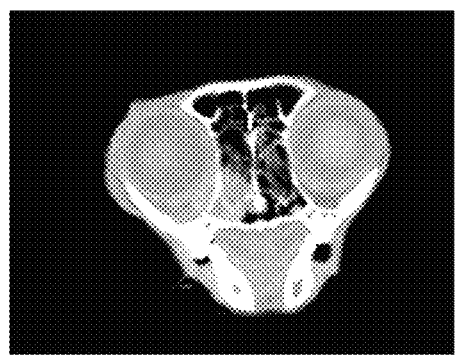
FIG. 29 is a CT photograph (on the 7th day of the 2nd course) of a cat (intranasal lymphoma).
Figure 30:
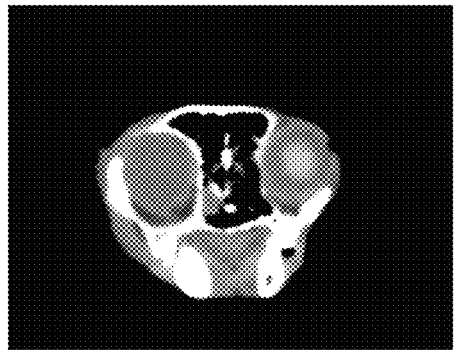
FIG. 30 is a CT photograph (on the 5th day after the end of the 2nd course) of a cat (intranasal lymphoma).

Treatment Regimen Featuring One Course Per 2 Weeks
Day 1 (Monday); LP-ICG-11 administration
Day 1 (Monday); near-infrared light irradiation (Super Lizer, Hyper 5000 from Tokyo Iken Co., Ltd.)
Day 3 (Wednesday); near-infrared light irradiation (Super Lizer, Hyper 5000 from Tokyo Iken Co., Ltd.)
Day 5 (Friday); near-infrared light irradiation (Super Lizer, Hyper 5000 from Tokyo Iken Co., Ltd.)
Day 8 (Monday); near-infrared light irradiation (Super Lizer, Hyper 5000 from Tokyo Iken Co., Ltd.)
Day 10 (Wednesday); near-infrared light irradiation (Super Lizer, Hyper 5000 from Tokyo Iken Co., Ltd.)
Day 12 (Friday); near-infrared light irradiation (Super Lizer, Hyper 5000 from Tokyo Iken Co., Ltd.)
Course of Treatment (FIGS. 25 and 26)

Course 1; Self-defecation became possible (PR; Partial Response) (FIG. 25).
Course 2; A state of remission was kept (SD; Stable Disease) (FIG. 26).

As a result of consultation with its owner, the volume reduction of the lymph node tumor was performed by surgery, but the dog died on the following day.

Treatment Result

It turned out that the anti-cancer effect of LP-ICG-11 shrank the tumor to make self-defecation possible to improve QOL and enabled a state of remission to be kept over a long period of time.

The results suggesting improved QOL and efficacy in palliative treatment were obtained.

(9-d) Cat; Nasal Cavity/Orbit Tumor (Lymphoma)

The anti-cancer effect of LP-ICG-11 was examined in a cat with nasal cavity/orbit tumor (cat species: crossbred, age: 15 years old).

Treatment Method

LP-ICG-11 (containing 17.5 mg) was administered by intravenous injection, and treatment was carried out using the following protocol.

Treatment Regimen Featuring One Course Per 2 Weeks

Day 1 (Monday); LP-ICG-11 administration

Day 1 (Monday); near-infrared light irradiation (DVL-30D from Asuka Medical Inc.)

Day 3 (Wednesday); near-infrared light irradiation (DVL-30D from Asuka Medical Inc.)

Day 5 (Friday); near-infrared light irradiation (DVL-30D from Asuka Medical Inc.)

Day 8 (Monday); near-infrared light irradiation (DVL-30D from Asuka Medical Inc.)

Day 10 (Wednesday); near-infrared light irradiation (DVL-30D from Asuka Medical Inc.)

Day 12 (Friday); near-infrared light irradiation (DVL-30D from Asuka Medical Inc.) Course of Treatment (FIGS. 27 to 30)

Course 1; Disease progressed (PD; Progression Disease).

Course 2; A state of remission was kept (SD; Stable Disease).

Course 3; A therapeutic effect was observed (PR; Partial Response).

Treatment Result

Combination with high concentration vitamin C therapy, Maruyama vaccine therapy, and ozone therapy from the course 1 made the anti-cancer effect of LP-ICG-11 noticeable and produced an effective therapeutic effect.

(9-e) Dog; Kidney Tumor

The anti-cancer effect of LP-ICG-11 was examined in a dog with kidney tumor (dog species: chihuahua, age: 5 years old).

Treatment Method

LP-ICG-11 (containing 17.5 mg) was administered by intravenous injection, and treatment was carried out using the following protocol.

Treatment Regimen Featuring One Course Per 2 Weeks

Day 1 (Monday); LP-ICG-11 administration

Day 2 (Tuesday); near-infrared light irradiation (800 nm LED light, 0.25 W/m$^2$, 20 minutes)

Day 5 (Friday); near-infrared light irradiation (800 nm LED light, 0.25 W/m$^2$, 20 minutes)

Day 9 (Tuesday); near-infrared light irradiation (800 nm LED light, 0.25 W/m$^2$, 20 minutes)

Day 12 (Friday); near-infrared light irradiation (800 nm LED light, 0.25 W/m$^2$, 20 minutes)

Course of Treatment

Course 1; A state of remission was kept (SD; Stable Disease).

Course 2; A state of remission was kept (SD; Stable Disease).

Course 3; A state of remission was kept (SD; Stable Disease).

Figure 31:
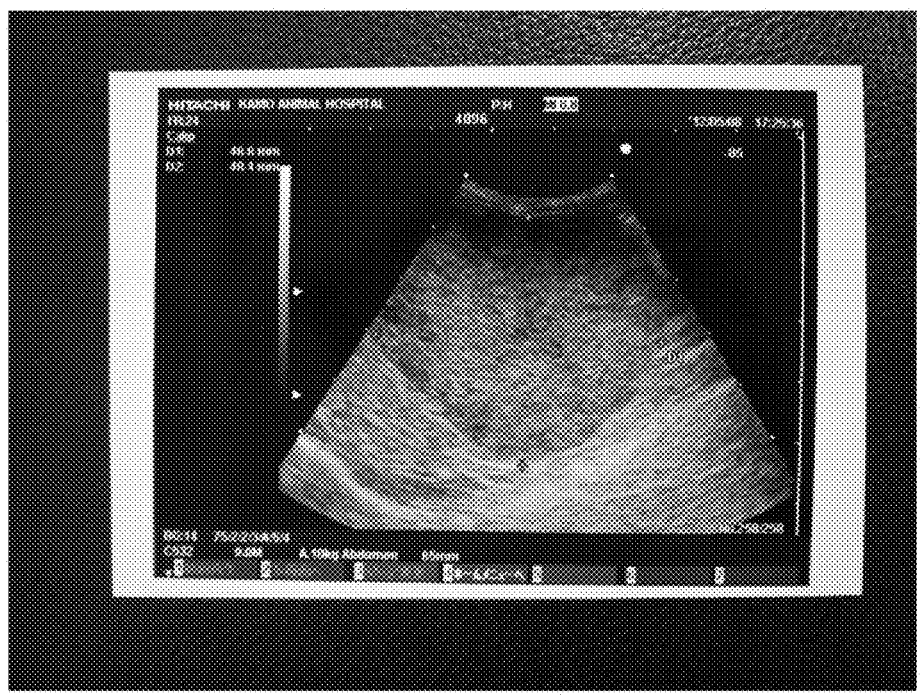
FIG. 31 is a pair of echo images of kidney tumor (upper: before treatment, lower: at the 4th course).
Figure 31:
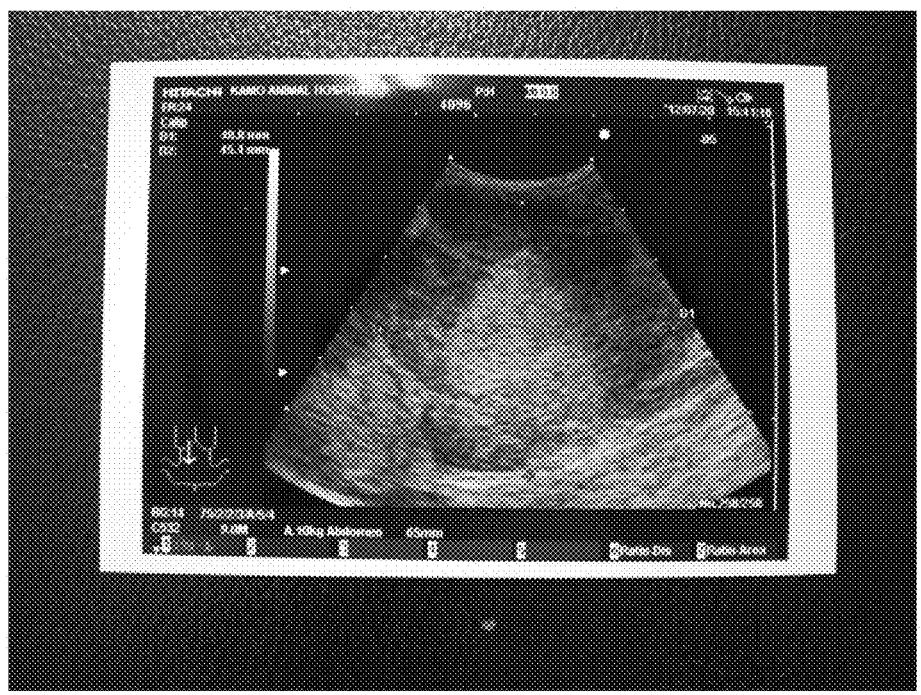

Course 4; The low echo area was expanded and thus a therapeutic effect was confirmed to have appeared (FIG. 31).

Improved symptoms were also noted from the results of blood examination (Table 3) (PR; Partial Response).

Treatment Result

The anti-cancer effect of LP-ICG-11 shrank kidney tumor and improved health status. An effective therapeutic effect, but not a complete cure, was produced.

TABLE 3

Result of Blood Examination for Kidney Tumor

| | Course 1 | Course 2 | Course 3 | Course 4 |
|---|---|---|---|---|
| Wbc | 277 | 128 | 96 | 101 × 10$^2$/μL |
| Rbc | 689 | 616 | 553 | 612 × 10$^4$/μL |
| Hgb | 13.3 | 12.1 | 10.6 | 11.6 g/dl |
| Hct | 43.6 | 39.2 | 35.3 | 39.9% |
| Mcv | 63.3 | 63.6 | 63.8 | 63.6 fL |
| Mch | 19.3 | 19.6 | 19.2 | 19.0 pg |
| Mchc | 30.5 | 30.9 | 30.0 | 29.8 g/dL |
| Plt | 62.1 | 69.7 | 49.3 | 28.9 × 10$^4$/μL |
| Ly | 26 | 25 | 29 | 19 |
| Mo | | 9 | 7 | 4 |
| Eo | | | 1 | 1 |
| Gr | 251 | 94 | 59 | 77 |

(9-f) Dog; Soft Tissue Sarcoma

The anti-cancer effect of LP-ICG-11 was examined in a dog with soft tissue sarcoma in the right forearm (dog species: crossbred, age: 6 years old).

History of Disorder

The surgical removal of soft tissue sarcoma in the right forearm was carried out.

Photothermal therapy by the local injection of ICG was performed weekly for 2 months and once every 2 weeks for 2 months; thereafter when the next course was attempted to be carried out, recurrence occurred; and thus, the surgical removal was again performed (incomplete removal).

Treatment Method

LP-ICG-11 (containing 17.5 mg) was administered by intravenous injection, and treatment was carried out using the following protocol.

Treatment Regimen Featuring One Course Per 2 Weeks

Day 1 (Monday); LP-ICG-11 administration

Day 1 (Monday); near-infrared light irradiation (Super Lizer, Hyper 5000 from Tokyo Iken Co., Ltd.)

Day 3 (Wednesday); near-infrared light irradiation (Super Lizer, Hyper 5000 from Tokyo Iken Co., Ltd.)

Day 5 (Friday); near-infrared light irradiation (Super Lizer, Hyper 5000 from Tokyo Iken Co., Ltd.)

Day 8 (Monday); near-infrared light irradiation (Super Lizer, Hyper 5000 from Tokyo Iken Co., Ltd.)

Day 10 (Wednesday); near-infrared light irradiation (Super Lizer, Hyper 5000 from Tokyo Iken Co., Ltd.)

Day 12 (Friday); near-infrared light irradiation (Super Lizer, Hyper 5000 from Tokyo Iken Co., Ltd.)

Figure 32:
FIG. 32 is a series of photographs showing the course of treatment of soft tissue sarcoma of a dog (left: a small tumor mass at the 4th course, middle: the ulcerated tumor mass at the first half of the 5th course, right: the necrotized tumor mass at the second half of the 5th course)

Course of Treatment (FIG. 32)

Course 1; A state of remission was kept (SD; Stable Disease).

Course 2; A state of remission was kept (SD; Stable Disease).

Course 3; A state of remission was kept (SD; Stable Disease).

Course 4; A small tumor mass appeared in the proximal suture-form skin subjected to re-surgery and was gradually enlarged (PD; Progression Disease).

Course 5; The small tumor mass was ulcerated, further enlarged, and then necrotized (PR; Partial Response).

Treatment Result

The anti-cancer effect of LP-ICG-11 induced necrosis in the soft tissue sarcoma; an effective therapeutic effect, but not a complete cure, was produced.

All publications, patents, and patent applications cited in this specification are intended to be incorporated herein by reference in their entirety.

INDUSTRIAL APPLICABILITY

According to the present invention, a drug delivery system can be provided which can sustainedly release the drug noninvasively at any given point in time.

The invention claimed is:

1. A method for treating a tumor comprising:
administering to a subject in need thereof an effective amount of a liposome comprising an anti-cancer agent and a liposome membrane-constituting substance, wherein the liposome membrane-constituting substance is (a) anchored in the hydrophobic membrane region of a liposome and (b) covalently bonded to a light-absorbing compound having an absorption wavelength in the near-infrared region, the light-absorbing compound comprising an indocyanine green dye, the anti-cancer agent being contained in the liposome; and irradiating an affected area of the subject with light; wherein the liposome membrane-constituting substance covalently bonded to the light-absorbing compound is represented by formula (I) below:

$$A\text{-}(CH_2)_a\text{-}B_1\text{-}(CH_2)_b\text{-}B_2\text{-}D\text{-}E_1 \qquad (I)$$

wherein A represents the light-absorbing compound;
$B_1$ and $B_2$ each independently represent —$CH_2$—, —CH=CH—, —O—, —S—, —NH—, —CO—, —COO—, —OCO—, —NHCO—, —CONH—, —$PO_4H$—, or —$PO_4M$- (where M represents an alkali metal ion);
D represents —$CHE_2$-, —$CH_2CH(OCOE_2)$-$CH_2OCO$—, or —$CHE_2$-$CH_2OCO$—;
$E_1$ represents a substituted or unsubstituted hydrocarbon group having 8 to 18 carbon atoms;
$E_2$ represents hydrogen or a substituted or unsubstituted hydrocarbon group having 8 to 18 carbon atoms; and
$a$ represents an integer of 0 to 4 and $b$ represents an integer of 0 to 6.

2. The method according to claim 1, comprising irradiating the affected area with light to generate singlet oxygen.

3. The method according to claim 1, wherein the liposome membrane-constituting substance comprises a lipid.

4. The method according to claim 1, wherein $B_1$ and $B_2$ each independently represent —$CH_2$—, —CH=CH—, —O—, or —S—; and D represents —$CHE_2$- (where $E_2$ is as described in claim 1).

5. The method according to claim 1, wherein $B_1$ and $B_2$ each represent —$CH_2$—.

6. The method according to claim 1, wherein the liposome membrane-constituting substance comprises at least one selected from the group consisting of lipids, membrane stabilizers, antioxidants, and membrane proteins.

7. The method according to claim 1, wherein the liposome membrane-constituting substance covalently bonded to the light-absorbing compound is represented by formula (II-1) below:

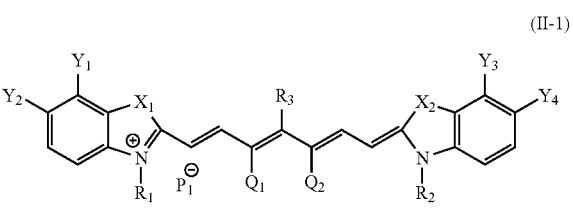

(II-1)

wherein $X_1$ and $X_2$ each represent —$C(CH_3)_2$—, O, or S; $Y_1$ and $Y_3$ each represent hydrogen or $OCH_3$ and $Y_2$ and $Y_4$ each represent hydrogen, or $Y_1$ and $Y_2$, and $Y_3$ and $Y_4$ each optionally together form a benzene ring fused with a ring to which they are bound; $Q_1$ and $Q_2$ each represent hydrogen or are optionally bonded to form a 6-membered ring; any one of $R_1$ to $R_3$ represents —$(CH_2)_a$-$B_1$-$(CH_2)_b$-$B_2$-D-$E_1$ where the symbols have the same meaning as those in the formula (I) in claim 1; $P_1$ represents chloride ion, bromide ion, or iodide ion as a monovalent anion; and $R_1$ to $R_3$ each represent a group selected from the group consisting of the following groups:

—$(CH_2)_nCH_3$  —$(CH_2)_nSH$  —$(CH_2)_nOH$

—$(CH_2)_nNH_2$  —$(CH_2)_nSO_3(M)$  —$(CH_2)_nCOO(M)$

—$(CH_2)_nPO_4(M)$  —$(CH_2)_n(CH_2CH_2O)_xH$

—$(CH_2)_nZ_1(CH_2)_mCH_3$  —$(CH_2)_nZ_1(CH_2)_mSH$

—$(CH_2)_nZ_1(CH_2)_mSH$

—$(CH_2)_nZ_1(CH_2)_mOH$  —$(CH_2)_nZ_1(CH_2)_mNH_2$

—$(CH_2)_nZ_1(CH_2)_mSO_3(M)$  —$(CH_2)_nZ_1(CH_2)_mCOO(M)$

—$(CH_2)_nZ_1(CH_2)_mPO_4(M)$  —$(CH_2)_nZ_1(CH_2CH_2O)_xH$

—$(CH_2)_nZ_1(CH_2CH_2O)_xH$  —$(CH_2)_nPO_4(CH_2)_mCH_3(M)$

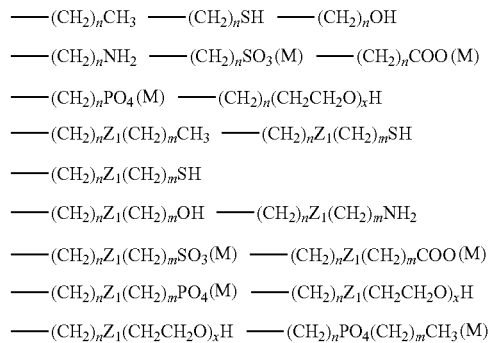

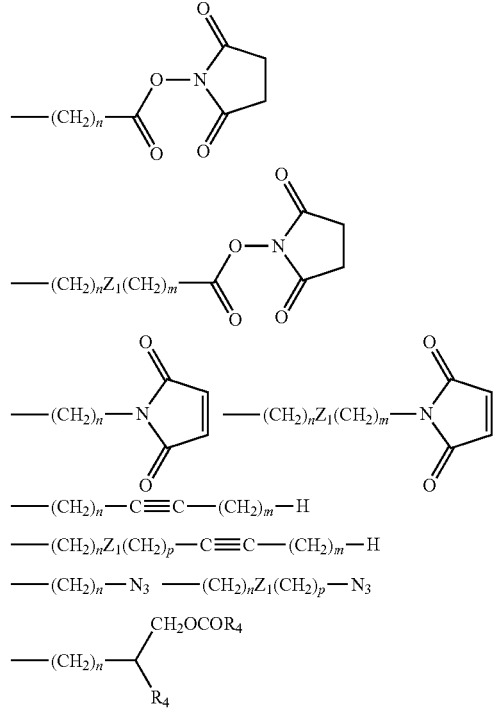

—$(CH_2)_n$—C≡C—$(CH_2)_m$—H

—$(CH_2)_nZ_1(CH_2)_p$—C≡C—$(CH_2)_m$—H

—$(CH_2)_n$—$N_3$  —$(CH_2)_nZ_1(CH_2)_p$—$N_3$

-continued

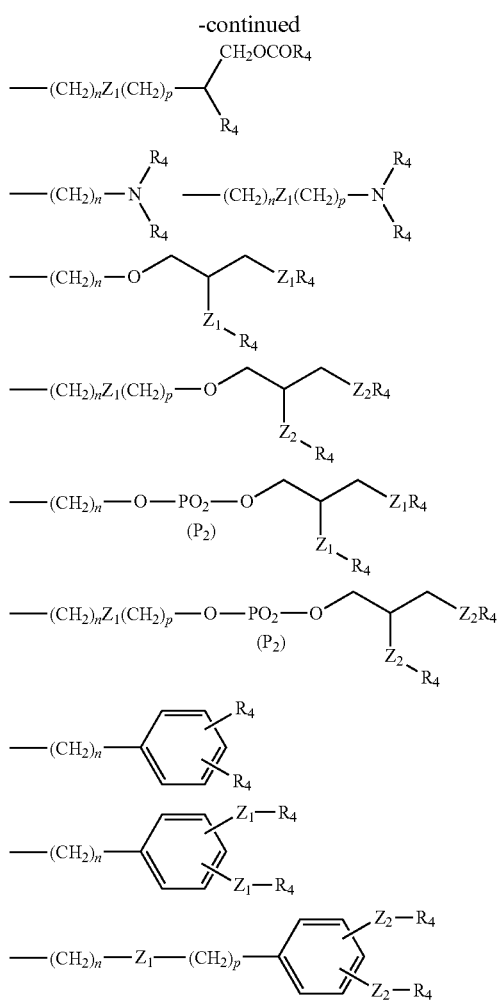

where $Z_1$ or $Z_2$ represents —O—, —NH—, —S—, —SO$_2$—, —CH=CH—, —SO$_2$NH—, —NHSO$_2$—, —CONH—, —NHCO—, —CO—, —COO—, —OCO—, or —C$_6$H$_4$—; P$_2$ represents hydrogen ion, lithium ion, sodium ion, or potassium ion as a monovalent cation; M represents hydrogen ion, lithium ion, sodium ion, or potassium ion as a monovalent cation; R$_4$ represents an alkane, an alkene, or an alkyne having 1 to 18 carbon atoms; n or m represents an integer of 0 to 22; l represents an integer of 1 to 22; p represents an integer of 0 to 17; and x represents an integer of 2 to 2,000.

8. The method according to claim 1, wherein the liposome membrane-constituting substance covalently bonded to the light-absorbing compound is represented by formula (5) below:

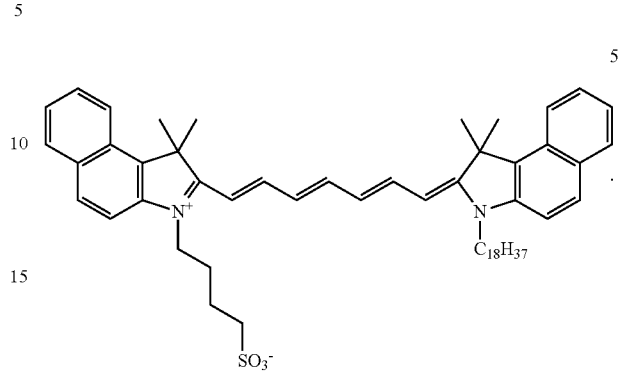

9. The method according to claim 1, wherein the liposome membrane-constituting substance covalently bonded to the light-absorbing compound is represented by the formula below:

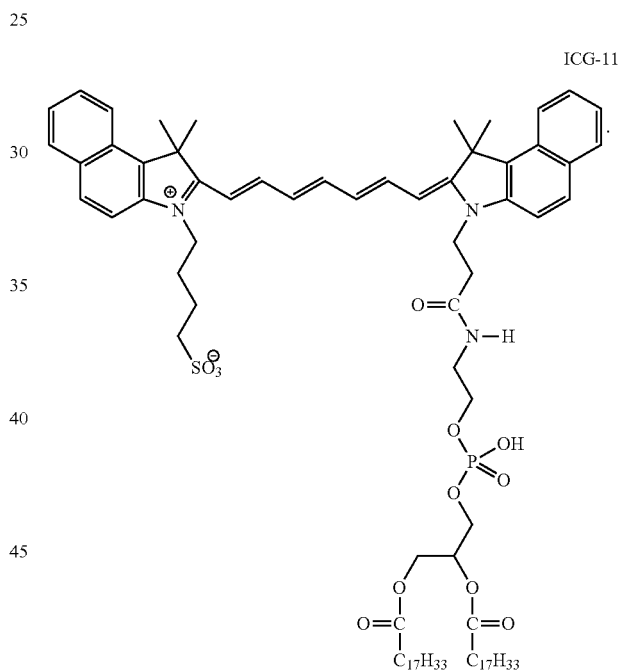

* * * * *